US012758531B2

(12) United States Patent
Stocker et al.

(10) Patent No.: US 12,758,531 B2
(45) Date of Patent: Oct. 13, 2026

(54) PHARMACEUTICAL COMPOSITIONS COMPRISING IONIC LIQUIDS

(71) Applicants: The Provost, Fellows, Foundation Scholars, and the other members of Board, of the College of the Holy and Undivided Trinity of Queen Elizabeth, near Dublin, Dublin (IE); UNIVERSITY COLLEGE DUBLIN, NATIONAL UNIVERSITY OF IRELAND, DUBLIN, Dublin (IE)

(72) Inventors: Michael Stocker, Dublin (IE); Steven Ferguson, Dublin (IE); Anne Marie Healy, Dublin (IE)

(73) Assignees: UNIVERSITY OF COLLEGE DUBLIN, Dublin (IE); The Provost, Fellows, Foundation Scholars, and the other members of board, of the College of the Holy and Undivided Trinity of Queen Elizabeth, near Dublin, Dublin (IE)

( * ) Notice: Subject to any disclaimer, the term of this patent is extended or adjusted under 35 U.S.C. 154(b) by 731 days.

(21) Appl. No.: 18/021,460

(22) PCT Filed: Aug. 9, 2021

(86) PCT No.: PCT/EP2021/072148
§ 371 (c)(1),
(2) Date: Feb. 15, 2023

(87) PCT Pub. No.: WO2022/037982
PCT Pub. Date: Feb. 24, 2022

(65) Prior Publication Data
US 2023/0338338 A1 Oct. 26, 2023

(30) Foreign Application Priority Data
Aug. 18, 2020 (GB) ..................................... 2012897

(51) Int. Cl.
*A61K 31/4164* (2006.01)
*A61K 9/16* (2006.01)
(Continued)

(52) U.S. Cl.
CPC ........ *A61K 31/4164* (2013.01); *A61K 9/1635* (2013.01); *A61K 9/1652* (2013.01); *A61K 31/14* (2013.01); *A61K 31/37* (2013.01)

(58) Field of Classification Search
CPC .. A61K 31/4164; A61K 31/14; A61K 9/1635; A61K 9/1652; A61K 41/64; C07D 233/158; C07D 311/156
See application file for complete search history.

(56) References Cited

U.S. PATENT DOCUMENTS 4,003,846 A 1/1977 Kuhn et al.
9,278,134 B2 3/2016 Rogers et al.
(Continued)

FOREIGN PATENT DOCUMENTS

CN 110386869 A 10/2019
DK 2432455 T3 2/2015
(Continued)

OTHER PUBLICATIONS

Jouannin et al , Drug Delivery Systems Based On Pharmaceutically Active Ionic Liquids and Biocompatible Poly(Lactic Acid)<Journal of Material Chemistry, B, vol. 2, No. 20., pp. 3133-3141. (Year: 2014).*
(Continued)

*Primary Examiner* — Carlos A Azpuru
(74) *Attorney, Agent, or Firm* — Hoffman Warnick LLC

(57) ABSTRACT

A composition comprising a polymer and a salt of a pharmaceutical compound, wherein the salt is an ionic liquid is
(Continued)

described. A solid dosage form comprising such a composition, and a method of preparing the composition are also described.

10 Claims, 29 Drawing Sheets

(51) Int. Cl.
*A61K 31/14* (2006.01)
*A61K 31/37* (2006.01)

(56) References Cited

U.S. PATENT DOCUMENTS

| | | | |
|---|---|---|---|
| 2016/0120983 A1 | 5/2016 | Hwang et al. |
| 2018/0169033 A1 | 6/2018 | Aoyagi et al. |

FOREIGN PATENT DOCUMENTS

| | | | |
|---|---|---|---|
| GB | 983065 A | 2/1965 |
| WO | 98001165 A1 | 1/1998 |
| WO | 2010078300 A1 | 7/2010 |
| WO | 2015013772 A1 | 2/2015 |
| WO | 2015066647 A2 | 5/2015 |

OTHER PUBLICATIONS

Jouannin et al, Durg Delivery Systems Based on Pharmaceutically Active Ionic Liquids and Biocompatible Poly(lactic acid)<Journal of Materials Chemistry B, 2, 3133-3141 (Year: 2014).*

Chantereau et al, Design of Anti-Inflammatory Drug-Based Ionic Liquids with Improved Water Solubility and Drug Delivery, ACS Sustainable Chemistry Engineering, vol. 7, No. 16, pp. 14126-14134. (Year: 2019).*

PCT International Search Report and Written Opinion for International Application No. PCT/EP2021/072148, dated Nov. 26, 2021, 15 pages.

Jouannin et al., "Drug delivery systems based on pharmaceutically active ionic liquids and biocompatible poly(lactic acid)," Journal of Materials Chemistry B, 2014, 2, pp. 3133-3141.

Chantereau et al., "Design of Nonsteroidal Anti-Inflammatory Drug-Based Ionic Liquids with Improved Water Solubility and Drug Delivery," ACS Sustainable Chemistry Engineering, vol. 7, No. 16, 2019, pp. 14126-14134.

Carquigny et al., "Investigation of pharmaceutically active ionic liquids as electrolyte for the electrosynthesis of polypyrrole and active component in controlled drug delivery," Elecrochimica Acta, vol. 211, 2016, pp. 950-961.

Egorova K. et al., "Biological Activity of Ionic Liquids and Their Application in Pharmaceutics and Medicine," Chemical Reviews, vol. 117, No. 10, 2017, pp. 7132-7189.

Maneewattanapinyo et al, "Controlled Release of Lidocaine-Diclofenac Ionic Liquid Drug from Freeze-Thawed Gelatin/Poly(Vinyl Alcohol) Transdermal Patches," AAPS PharmSciTech, Springer International Publishing, Cham, vol. 20, No. 8, 2019, 9 pages.

Serajuddin, "Salt formation to improve drug solubility," ScienceDirect, Advanced Drug Delivery Reviews, Elsevier, vol. 59, No. 7, 2007, pp. 603-616.

Stocker et al., "Spray Encapsulation as a Formulation Strategy for Drug-Based Room Temperature Ionic Liquids: Exploiting Drug-Polymer Immiscibility to Enable Processing for Solid Dosage Forms," Molecular Pharmaceutics, vol. 17, No. 9, 2020, pp. 3412-3424.

Egorova et al., "Cytotoxic Activity of Salicylic Acid-Containing Drug Models with Ionic and Covalent Binding," ACS Medicinal Chemistry Letters, vol. 6, 2015, pp. 1099-1104.

Balk et al., "Transformation of acidic poorly water soluble drugs into ionic liquids," European Journal of Pharmaceutics and Biopharmaceutics, vol. 94, 2015, pp. 73-82.

M. Fuchs et al., "Encapsulation of oil in powder using spray drying and fluidised bed agglomeration," Elsevier, Journal of Food Engineering, Jul. 2006, pp. 27-35.

Seid Mahdi Jafari et al., "Nano-particle encapsulation of fish oil by spray drying," Elsevier, ScienceDirect, 2008, pp. 172-183.

Alysson Leandro Ribeiro Rattes et al., "Spray drying conditions and encapsulating composition effects on formation and properties of sodium diclofenac microparticles," Elsevier, ScienceDirect, Jan. 2007, pp. 7-14.

Re, "Microencapsulation by spray drying," Drying Technology, Apr. 27, 2007, pp. 1195-1236.

Stoimenovski et al., "Crystalline vs. Ionic Liquid Salt Forms of Active Pharmaceutical Ingredients: A Position Paper," Pharmaceutical Research, Feb. 9, 2010, pp. 521-526.

Guy Van den Mooter, "The use of amorphous solid dispersions: A formulation strategy to overcome poor solubility and dissolution rate," Elsevier, Drug Discovery Today: Technology, 2012, pp. e79-e85.

* cited by examiner

PHARMACEUTICAL COMPOSITIONS COMPRISING IONIC LIQUIDS

FIELD OF THE INVENTION

The present invention relates to a composition comprising a polymer and a pharmaceutical compound in the form of an ionic liquid, a solid dosage form comprising such a composition, and a method of preparing such a composition. In particular, the invention relates to a solid composition comprising a polymer and a pharmaceutical compound in the form of an ionic liquid.

BACKGROUND OF THE INVENTION

The preferred commercial route of administration for the majority of drugs/medicines is through oral solid dosage forms that utilise the most thermodynamically stable crystalline form of the Active Pharmaceutical Ingredient (API). These solid dosage forms are easy to administer and have a long shelf life. However, thermodynamically stable crystalline forms have a high lattice enthalpy, corresponding to poor solubility of the API in aqueous solutions, and poor bioavailability in the gastrointestinal (GI) tract.

Amorphous forms and metastable crystalline polymorphs of APIs both lack the high level of order of the thermodynamically stable crystalline solid. As a result, the energy required to disrupt the solid phase is lower and the solubility of the API is increased. However, amorphous APIs are inherently thermodynamically unstable, meaning that they are likely to undergo crystal growth during storage and can also recrystallise in the GI tract upon dissolution, losing the benefits of increased solubility. Metastable APIs face similar problems.

Amorphous APIs are typically combined with polymer excipient(s) in an amorphous solid dispersion (ASD) in order to improve the stability of the API, both during storage and dissolution. However, a high ratio of polymer to API must often be used to avoid phase separation or crystallisation of the amorphous API. This limits the amount of API that can feasibly be incorporated in a solid dosage form so that this approach may be unsuitable for certain APIs where the required dosage is high, or the therapy is intended for paediatric use, due to regulatory or consumer driven limits on tablet/capsule size. Additionally, while the amorphous form may initially appear to be stable, the stability of ASDs may deteriorate over time, especially when exposed to unfavourable storage conditions such as elevated temperature or humidity. This can result in the insoluble crystalline form of the API inadvertently being administered, which in turn may adversely affect bioavailability. Furthermore, on dissolution of ASDs, APIs are often initially released to very high levels before precipitating from solution over time, thereby decreasing performance over time.

Ionic liquids (ILs) exhibit unique combinations of characteristics that make them of interest across a wide and varied range of applications. Among these are good thermal stability, negligible vapour pressure, and powerful solvation properties that can be tuned by selection of anion/cation pairs. The large amount of possible ion pairs means that ILs are often described as 'designer' compounds which can be adjusted to perform within exacting criteria. ILs typically have low melting points compared to conventional salts such as sodium chloride (NaCl), which can be attributed to their very different chemical structures. While sodium chloride (NaCl), for example, is composed of two small spherical inorganic atoms, ILs instead typically contain at least one bulky asymmetric organic ion. This bulky structure makes it difficult for the ions to arrange themselves in a well ordered structure and pack closely together, preventing crystallisation. This means that the lattice enthalpy of ILs is very small in comparison to conventional salts, which is reflected in the comparatively low melting points. For example, the IL 1-butyl-1-methylpyrrolidinium bis(trifluoromethylsulfonyl) imide melts at −18° C. in contrast to NaCl which melts at 803° C.

The molecular structures of many APIs exhibit properties that are favourable for forming ILs without the need for further modification. API are almost always organic molecules and the vast majority are large, asymmetric and contain aromatic groups, all of which are desirable when forming ILs. In addition to this, formulating APIs as salts is an established approach to overcoming undesirable physicochemical properties, with approximately 50% of drugs/medicines on the market sold as salts in the final dosage form. The IL approach can also be applied to cases where the API is not currently formulated as a salt, as it has been estimated that approximately 63% of APIs contain ionisable groups. As the liquid form of the IL is the most thermodynamically stable physical form, forming ILs where at least one of the ions is an API would avoid the problems associated with ASDs. However, ILs are generally difficult materials to work with as most that are liquid at room temperature exist as viscous oils, making handling, processing and formulation for oral solid administration problematic.

Formulation of APIs as liquids is normally achieved by encapsulation in hard or soft capsules. However, encapsulation is a time-consuming batch process which can take from several hours to several days. Encapsulation also takes place at relatively low temperatures (typically about 40° C. for soft capsules and about 70° C. for hard capsules), making it challenging to overcome any viscosity limitations of the API-containing liquid. Additionally, it is also significantly harder to control the release of the API when in this encapsulated form. To mitigate this, it has been shown that the IL can been combined with other materials such as ionogels or mesoporous silica to trap it in a solid phase. However, it has also been shown that formulating liquid APIs in mesoporous silica can severely hinder the bioavailability of the API by as much as 50% in comparison to the equivalent free liquid, as a result of incomplete desorption from the solid carrier. This can be further exacerbated by the in situ formation of gels on exposure to the dissolution medium which results in the pores being blocked and hindering release.

SUMMARY OF THE INVENTION

It is one aim of the present invention, amongst others, to provide a dosage form that addresses at least one disadvantage of the prior art, whether identified here or elsewhere, or to provide an alternative to existing dosage forms. For instance, it may be an aim of the present invention to provide a solid dosage form which has high stability and bioavailability.

According to aspects of the present invention, there is provided a composition, a solid dosage form, and a method as set forth in the appended claims. Other features of the invention will be apparent from the dependent claims, and the description which follows.

According to a first aspect of the present invention, there is provided a composition comprising a polymer and a salt of a pharmaceutical compound, wherein the salt is an ionic liquid.

The inventors have found that it is possible to formulate pharmaceutical compounds in the form of an ionic liquid into compositions (such as solid compositions) by combining the ionic liquid with a polymer. These compositions have the advantages of long-term thermodynamic stability and bioavailability associated with ionic liquids.

The compositions of the present invention may be solid compositions at room temperature. By the term "solid composition" we mean a composition that can be handled and formulated as a solid. Such solid compositions include two-phase compositions, for example that may comprise some liquid, but which can be handled and formulated as a solid. Such solid compositions offer advantages in use of ease of handling and administration as typically associated with solid compositions.

The composition may be in any suitable solid form. For example, the composition may be in the form of a powder.

Any suitable polymer may be included in the compositions of the present invention.

Suitable polymers may be selected from a polysaccharide, a polysaccharide derivative, a polyvinyl ester (such as polyvinyl acetate), an aliphatic polyester (such a poly(glycolic acid) and copolymers thereof), a polyester (such as polycaprolactone), shellac, a (meth)acrylic acid based polymer, and mixtures thereof.

Examples of suitable copolymers of poly(glycolic acid) include, for example, poly(lactic-co-glycolic acid, poly(glycolide-co-caprolactone) and poly (glycolide-co-trimethylene carbonate).

Examples of suitable polysaccharides include maltodextrin and sodium alginate. Preferably, the polysaccharide comprises maltodextrin.

Examples of suitable polysaccharide derivatives include cellulose derivatives, such as a cellulose ester (such as cellulose acetate, cellulose acetate phthalate, and cellulose acetate butyrate,) or cellulose ether (such as methyl cellulose, ethyl cellulose, hydroxypropyl methylcellulose, hydroxyethylcellulose, hydroxylpropyl cellulose, and carboxymethyl cellulose). Preferably, the cellulose derivative comprises ethyl cellulose.

Examples of suitable (meth)acrylic acid based polymers include poly(meth)acrylate, (meth)acrylic acid copolymers, ammonio methacrylate, ammonio methacrylate copolymer type A, ammonio methacrylate copolymer type B, methacrylic acid copolymer type A, methacrylic acid copolymer type B, methacrylic acid copolymer type C, amino dimethyl methacrylate copolymers and amino diethyl methacrylate copolymers.

As used herein and as conventional in the art, use of "(meth)acrylate", and like terms, refers to both methacrylate and acrylate.

Preferably, the polymer comprises a polysaccharide, a cellulose derivative, a (meth)acrylic acid based polymer, or a mixture thereof.

Suitable ethyl celluloses include, for example, Ethocel Standard 10 Premium and Ethocel Standard 4 Premium (from Dow Wolff Cellulosics GmbH., Bomlitz, Germany).

Suitable maltodextrins include, for example, Glucidex 6D and Glucidex 19D (from Roquette Frères, Lestrem, France).

A suitable methacrylic acid copolymer is, for example, Eudragit L100 (from Evonik Industries, Essen, Germany).

In some embodiments, the polymer is selected from maltodextrin, ethyl cellulose, a (meth)acrylic acid copolymer, and mixtures thereof.

In some embodiments the polymer is immiscible with the ionic liquid at room temperature. By this we mean that the polymer has sufficiently low solubility in the ionic liquid that the polymer and the ionic liquid exist as two phases within the composition. In such embodiments the polymer suitably encapsulates the ionic liquid, for instance by forming a matrix, solid phase support or surround in which the ionic liquid is held. The inventors have surprisingly found that the dissolution properties of an ionic liquid in such a system are not significantly affected by the polymer, even where the polymer itself does not fully dissolve in the dissolution medium. This is advantageous as it allows the composition to be formulated without negatively affecting the performance of the ionic liquid. These embodiments also allow the inclusion of polymers having lower glass transition temperatures than if the polymer and ionic liquid were intimately mixed, since the ionic liquid does not cause depression of the glass transition temperature of the polymer.

Suitable polymers that are selected as being immiscible with the ionic liquid at room temperature will, of course, depend on the particular ionic liquid being used. Typically, examples of suitable polymers that are immiscible with the ionic liquid at room temperature may be selected from a polysaccharide derivative, a polyvinyl ester (such as polyvinyl acetate), an aliphatic polyester (such as poly(glycolic acid) and copolymers thereof), a polyester (such as polycaprolactone), shellac, a (meth)acrylic acid based polymer, and mixtures thereof.

In other embodiments the polymer is miscible with the ionic liquid at room temperature. By this we mean that the polymer has sufficiently high solubility in the ionic liquid that the polymer and the ionic liquid form a single continuous phase within the composition. In such embodiments the polymer and the ionic liquid typically form a single phase solid dispersion or solid solution. Compositions comprising the polymer and the ionic liquid in a single phase may be particularly suitable for preparing a solid dosage form by a compression-based technique, such as roller compaction granulation or direct compression.

Suitable polymers that are selected as being miscible with the ionic liquid at room temperature will, of course, depend on the particular ionic liquid being used. Typically, suitable polymers that are miscible with the ionic liquid at room temperature include polysaccharides.

The polymer may have a glass transition temperature ($T_g$) of greater than 80° C., suitably greater than 100° C., for example greater than 150° C.

The polymer may have a glass transition temperature ($T_g$) of greater than 80° C., suitably greater than 100° C., for example greater than 150° C., and may be miscible with the ionic liquid at room temperature.

The polymer may have a glass transition temperature ($T_g$) of less than 80° C., suitably less than 60° C., for example less than 20° C.

The polymer may have a glass transition temperature ($T_g$) of less than 80° C., suitably less than 60° C., for example less than 20° C., and may be immiscible with the ionic liquid at room temperature.

The polymer may be substantially insoluble in water at room temperature, by which we mean that no more than 1 g of the polymer will dissolve in 1,000 ml of water. The polymer may be substantially insoluble in water at 37° C. A suitable example of a polymer which is substantially insoluble in water at room temperature is ethyl cellulose.

Alternatively, the polymer may be soluble in water at room temperature, by which we mean that 1 g of the polymer will dissolve in in 30 ml or less of water. The polymer may be soluble in water at 37° C. A suitable example of a polymer which is soluble in water at room temperature is maltodextrin.

By the term "room temperature" we mean a temperature of from 15 to 30° C., suitably from 20 to 25° C., for example about 20° C.

Any suitable pharmaceutical compound may be included in the compositions of the present invention, provided that it can be provided as a salt in the form of an ionic liquid.

By the term "pharmaceutical compound" we mean a chemical compound that has pharmaceutical activity, for example so as to be effective to treat or prevent a disease or symptom in a warm-blooded animal such as a human. The pharmaceutical compound may alternatively be defined as an active pharmaceutical ingredient (API).

By the term "ionic liquid" we mean a salt (i.e. a salt of the pharmaceutical compound) that melts below 100° C. The ionic liquid may have a melting point of less than 100° C., suitably less than 40° C., for example less than 25° C. Suitably, the ionic liquid is liquid at room temperature. The ionic liquid may be liquid at 37° C. The ionic liquid may be alternatively defined as a molten salt or a lipophilic salt.

The ionic liquid is a salt of a pharmaceutical compound having an ionisable group. Suitable ionisable groups include carboxylic acid groups, hydroxyl groups, and amine groups.

Examples of suitable pharmaceutical compounds having an ionisable group include ibuprofen, warfarin and propranolol.

The ionic liquid comprises an ion of the pharmaceutical compound and a counterion. Suitably, the counterion is pharmaceutically acceptable. In embodiments where the ion of the pharmaceutical compound is a cation, the counterion is an anion. In embodiments where the ion of the pharmaceutical compound is an anion, the counterion is a cation. The counterion may be an organic ion. The counterion may comprise at least 4, suitably at least 5, for example at least 6 carbon atoms. In some embodiments the counterion is selected from 1-butyl-3-methyl imidazolium, choline, and saccharin. In some embodiments, the counterion may be the ion of another pharmaceutical compound. In such embodiments the ionic liquid comprises the ions of two or more different pharmaceutical compounds.

Methods of forming ionic liquids will be known to those skilled in the art. Such methods include acid-base neutralisation or the reaction of two or more salts. For example, the ionic liquid may be formed by reacting together a first salt and a second salt, wherein the first salt comprises the ion of the pharmaceutical compound, and the second salt comprises the counterion of the ionic liquid. For example, the first salt and the second salt comprise inorganic ions (such as sodium and chloride) that combine to form an inorganic salt. This inorganic salt can then be separated from the ionic liquid.

Examples of suitable ionic liquids include 1-butyl-3-methyl imidazolium ibuprofenate, choline ibuprofenate, 1-butyl-3-methyl imidazolium warfarinate, choline warfarinate, and propranolol saccharin.

The ionic liquid may be soluble in aqueous media over a pH range of 1 to 6.8 at 37±1° C. The ionic liquid comprising a single therapeutic dose of the pharmaceutical compound is suitably completely soluble in 250 mL or less of aqueous media over a pH range of 1 to 6.8 at 37±1° C. Preferably, the ionic liquid has high solubility as per the Biopharmaceutics Classification System. For example, the ionic liquid may be classified as Class 1 or Class 3 according to the Biopharmaceutics Classification System.

The free acid or free base of the pharmaceutical compound may be insoluble in aqueous media over a pH range of 1 to 6.8 at 37±1° C. A single therapeutic dose of the free acid or free base of the pharmaceutical compound is suitably not completely soluble in 250 mL or less of aqueous media over a pH range of 1 to 6.8 at 37±1° C. Preferably, the free acid or free base of the pharmaceutical compound has low solubility as per the Biopharmaceutics Classification System. For example, the free acid or free base of the pharmaceutical compound may be classified as Class 2 or Class 4 according to the Biopharmaceutics Classification System.

For avoidance of doubt, the free acid of the pharmaceutical compound corresponds to the unionised form of the pharmaceutical compound where the pharmaceutical compound is present as an anion in the ionic liquid. The free base of the pharmaceutical compound corresponds to the unionised form of the pharmaceutical compound where the pharmaceutical compound is present as a cation in the ionic liquid.

The weight ratio of the ionic liquid to the polymer in the composition may be from 10:90 to 90:10, suitably from 25:75 to 90:10, for example from 40:60 to 90:10.

Suitably, the composition comprises solvents in an amount of less than 10 wt %, suitably less than 5 wt %, for example less than 1 wt % based on the total weight of the composition. The composition may be substantially free of solvents. By "substantially free" we mean that solvents, if present, are only present in trace amounts (i.e. less than 0.1 wt %, preferably less than 0.01 wt % based on the total weight of the composition). In some embodiments, the composition is completely free of solvents.

The composition may comprise the ionic liquid and the polymer in separate phases, for example at room temperature. In this embodiment the ionic liquid is suitably encapsulated by the polymer, which may be in the form of a matrix, solid phase support or surround. It may be determined that the composition comprises the ionic liquid and the polymer in separate phases by the presence of one or more transition temperatures (such as a glass transition temperature or a melting point) in a differential scanning calorimetry (DSC) thermogram within ±5° C. of transition temperatures of the pure ionic liquid and/or the pure polymer.

Alternatively, the composition may comprise the ionic liquid and the polymer in a single phase, for example as a single phase solid dispersion or solid solution. The single phase solid dispersion or solid solution may have a glass transition temperature of at least 60° C., suitably at least 80° C., for example at least 100° C. The glass transition temperature of the dispersion is typically in between the melting point or glass transition temperature of the ionic liquid and the glass transition temperature of the polymer.

According to a second aspect of the present invention, there is provided a solid dosage form comprising the composition of the first aspect. Preferably, the solid dosage form is an oral solid dosage form.

The suitable features and advantages of the ionic liquid and the polymer of this second aspect are as defined in relation to the first aspect.

The solid dosage form may be in the form of a tablet, capsule, caplet, cachet, lozenge, film, granulate, beads, or powder.

The solid dosage form may comprise the composition of the first aspect in the form of a loose powder or in a compacted form. For example, the solid dosage form may be a tablet comprising the composition of the first aspect in a compacted form.

The solid dosage form may be an immediate release dosage form or a modified release dosage form. In embodiments where the composition of the first aspect comprises the ionic liquid and the polymer in separate phases, the solid dosage form is suitably an immediate release dosage form. The modified release dosage form may suitably comprise an enteric coating. Suitably the enteric coating prevents the solid dosage form from disintegrating or dissolving at a pH of less than 3, for example less than 2.

The solid dosage form may comprise conventional pharmaceutical carriers or excipients known in the art. The solid dosage form may comprise conventional additional components, such as, for example, one or more glidants, disintegrants, binders, coating agents, colouring agents, sweetening agents, flavouring agents and/or preservative agents.

According to a third aspect of the present invention, there is provided a method of preparing the composition of the first aspect, comprising the steps of:

(a) forming a solution comprising a solvent, a salt of a pharmaceutical compound and a polymer, wherein the salt is an ionic liquid;

(b) removing the solvent from the solution to form a composition (preferably a solid composition) according to the first aspect.

The suitable features and advantages of the ionic liquid and the polymer of this third aspect are as defined in relation to the first aspect.

The inventors have found that pharmaceutical compounds in the form of an ionic liquids can be incorporated into a solid composition by removing the solvent from a solution comprising a pharmaceutical compound in the form of an ionic liquid and a polymer. This is advantageous because it results in stable compositions having good bioavailability of the pharmaceutical compound. The method of the invention further provides high loadings of the pharmaceutical compound in the composition, such as loadings of 50 wt % or higher.

The solvent may comprise an organic solvent, an aqueous solvent, or a mixture thereof. Suitable organic solvents include hydrocarbons (such as alkanes, alkenes, and aromatic compounds), alcohols, ethers, esters, ketones, and amides. The solvent may comprise an alcohol, such as methanol, ethanol, and/or propanol, preferably methanol. The solvent may have a boiling point of from 30 to 100° C., suitably from 40 to 90° C., for example from 50 to 80° C.

The concentration of the polymer in the solution in step (a) may be from 1 to 50% w/v, suitably from 1 to 30% w/v, for example from 1 to 10% w/v.

Step (b) of the method of the third aspect suitably comprises removing the solvent from the solution, suitably rapidly removing the solvent from the solution. Step (b) suitably comprises removing the solvent by vaporisation of the solvent.

Step (b) may comprise removing the solvent from the solution by spray drying, spray coating, electrospinning, electrospraying, or solvent casting the solution. Preferably, step (b) comprises spray drying the solution.

According to a fourth aspect of the present invention, there is provided a salt of 1-butyl-3-methyl imidazolium warfarinate, wherein the salt is an ionic liquid.

According to a fifth aspect of the present invention, there is provided a salt of choline warfarinate, wherein the salt is an ionic liquid.

According to a sixth aspect of the present invention, there is provided a salt of 1-butyl-3-methyl imidazolium ibuprofenate, wherein the salt is an ionic liquid.

According to a seventh aspect of the present invention, there is provided a salt of choline ibuprofenate, wherein the salt is an ionic liquid.

According to an eighth aspect of the present invention, there is provided a salt of propranolol saccharin, wherein the salt is an ionic liquid.

EXAMPLES

Example 1

Figure 1:
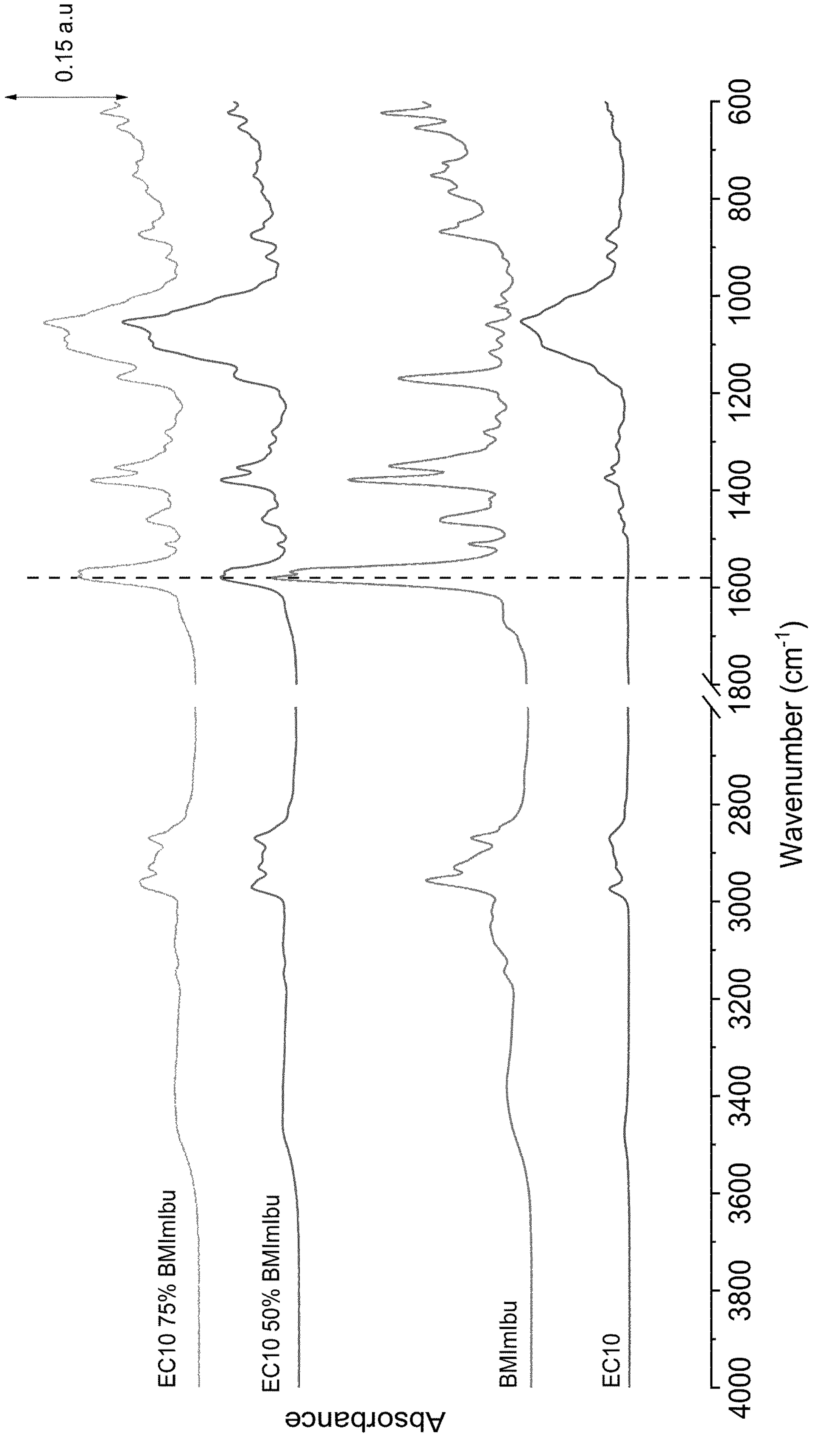
FIG. 1 shows IR spectra of 1-butyl-3-methyl imidazolium ibuprofenate (BMIm Ibu), Ethocel Standard 10 Premium (EC10), a spray dried powder comprising 50% w/w BMIm Ibu and 50% w/w EC10, and a spray dried powder comprising 75% w/w BMIm Ibu and 25% w/w EC10.

The general procedure for forming the pharmaceutical compound containing ionic liquids was as follows. Given amounts of the sodium salt of the anion and the chloride salt of the cation were dissolved separately in a specified amount of methanol. The solutions were then slowly combined and heated to 70° C. under reflux overnight. The reaction was then allowed to stir for another 12 hours at room temperature before being filtered through a sintered glass funnel (POR 3) under vacuum and the solvent removed under reduced pressure. The resulting ionic liquid was then washed with 50 mL of acetone and again filtered before being subsequently dried. This process was repeated a minimum of three times or until precipitation ceased.

$^1$H and $^{13}$C NMR spectra were obtained using a Varian VnmrS 300 MHz spectrometer. IR spectra for the pure ionic liquids and spray dried products were obtained using a Spectrum 1 FT-IR Spectrometer (Perkin Elmer, Connecticut, U.S.A) equipped with a Universal Attenuated Total Reflectance and diamond/ZnSe crystal accessory. Each spectrum was scanned in the range of 600-4000 cm$^{-1}$ with a resolution of 1 cm$^{-1}$.

1-butyl-3-methyl Imidazolium Ibuprofenate (BMIm Ibu) Ionic Liquid

The general procedure was applied to sodium ibuprofenate (40.000 g, 175.1620 mmol, 1 equiv.) in 200 mL methanol and 1-butyl-3-methyl imidazolium chloride (30.609 g, 175. mmol, 1 equiv.) in 100 mL methanol to produce 1-butyl-3-methyl imidazolium ibuprofenate as a viscous yellow liquid (47.960 g, 90%).

$^1$H NMR (300 MHz, $CDCl_3$): δ=10.60 (s, 1H), 7.27 (d, J=8.0 Hz, 2H), 7.12 (d, J=1.7 Hz, 1H), 7.06 (d, J=1.7 Hz, 1H), 6.94 (d, J=7.9 Hz, 2H), 4.08 (t, J=7.4 Hz, 2H), 3.78 (s, 3H), 3.54 (q, J=7.1 Hz, 1H), 2.34 (d, J=7.1 Hz, 2H), 1.85-1.62 (m, 3H), 1.41 (d, J=7.1 Hz, 3H), 1.25 (sext., J=7.4 Hz, 2H), 0.89 (d, J=7.3 Hz, 3H), 0.82 (d, J=6.6 Hz, 6H). $^{13}$C NMR (101 MHz, $CDCl_3$) δ=180.69, 142.67, 139.79, 138.57, 128.59, 127.42, 122.48, 120.83, 49.51, 49.17, 45.05, 36.16, 32.01, 30.21, 22.37, 19.62, 19.41, 13.40. $FTIR_{vmax}$ (cm$^{-1}$): 3383, 3052, 2957, 2869, 1581, 1462, 1379, 1170, 1059, 868, 753, 624.

The thermodynamic stability of BMIm Ibu (ionic liquid) in deionised water (DIW) and simulated intestinal fluid (SIF; 0.05 M phosphate buffer, pH 6.8) was quantified as follows: Ratios of 2 to 85% w/w BMIm Ibu:dissolution medium were placed in small vials and allowed to stir for 24 hours at 37° C. The samples were observed for potential crystallisation or liquid-liquid phase separation before being placed in a fume hood under ambient conditions and monitored over a period of two years. No crystallisation or phase separation was observed for either medium, with the solution remaining as a single aqueous phase throughout. This strongly indicates that BMIm Ibu is thermodynamically stable and fully miscible in both DIW and SIF.

1-butyl-3-methyl Imidazolium Warfarinate (BMIm War) Ionic Liquid

The general procedure was applied to sodium warfarinate (3.410 g, 10.3236 mmol, 1 equiv.) in 10 mL methanol and 1-butyl-3-methyl imidazolium chloride (1.8032 g, 10.3235 mmol, 1 equiv.) in 10 mL methanol to produce 1-butyl-3-methyl imidazolium warfarinate as a viscous colourless semi-liquid (3.049 g, 97.5%).

$^1$H NMR (300 MHz, $CDCl_3$) δ 9.35 (s, 1H), 7.90 (dd, J=7.8, 1.7 Hz, 1H), 7.47 (d, J=7.6 Hz, 2H), 7.31-7.21 (m, 1H), 7.06 (t, J=7.7 Hz, 2H), 7.03-6.98 (m, 2H), 6.97-6.91 (m, 3H), 5.02 (t, J=7.5 Hz, 1H), 3.86 (t, J=7.5 Hz, 2H), 3.66 (s, 4H), 3.26 (dd, J=15.8, 6.7 Hz, 1H), 2.12 (d, J=12.5 Hz, 5H), 1.62-1.52 (m, 2H), 1.14 (h, J=7.4 Hz, 2H), 0.80 (t, J=7.3 Hz, 3H). $^{13}$C NMR (101 MHz, $CDCl_3$) δ=207.20, 165.60, 154.09, 146.97, 137.87, 129.76, 128.97, 128.23, 128.04, 127.81, 125.25, 124.76, 123.18, 122.14, 121.65, 115.86, 100.16, 49.82, 47.08, 36.41, 36.34, 32.05, 31.12, 30.47, 19.54, 13.49. $FTIR_{vmax}$ ($cm^{-1}$): 3060, 2961, 1708, 1598, 1515, 1459, 1404, 1357, 1222, 1169, 1103, 1026, 960, 896, 759, 701, 623.

Choline Ibuprofenate (Cho Ibu) Ionic Liquid

The general procedure was applied to sodium ibuprofenate (10.000 g, 37.8372 mmol, 1 equiv.) in 30 mL methanol and choline chloride (6.1258 g, 43.8748 mmol, 1 equiv.) in 20 mL methanol to produce choline ibuprofenate as a white solid (13.0 g, 97%).

$^1$H NMR (300 MHz, Methanol-$d_4$) δ=7.29-7.24 (m, 2H), 7.03 (d, J=7.8 Hz, 2H), 4.01-3.95 (m, 2H), 3.54 (q, J=7.1 Hz, 1H), 3.46 (d, J=9.6 Hz, 2H), 3.19 (s, 10H), 2.42 (d, J=7.3 Hz, 2H), 1.82 (dt, J=13.5, 6.8 Hz, 1H), 1.39 (d, J=7.1 Hz, 3H), 0.88 (d, J=6.9 Hz, 7H). $^{13}$C NMR (101 MHz, Methanol-$d_4$) δ=183.35, 142.87, 140.28, 129.81, 128.33, 69.06, 69.03, 69.00, 57.04, 54.69, 54.65, 54.61, 50.01, 49.64, 49.60, 49.42, 49.21, 49.10, 49.00, 48.78, 48.57, 48.36, 46.09, 31.51, 22.71, 20.03. $FTIR_{vmax}$ ($cm^{-1}$): 3025, 2956, 2926, 2869, 1710, 1571, 1511, 1465, 1418, 1382, 1355, 1283, 1252, 1209, 1193, 1168, 1136, 1088, 1061, 1005, 955, 923, 870, 786, 752, 725, 671, 634.

Choline Warfarinate (Cho War) Ionic Liquid

The general procedure was applied to sodium warfarinate (5.0000 g, 15.1373 mmol, 1 equiv.) in 20 mL methanol and choline chloride (2.1114 g, 15.1225 mmol, 1 equiv.) in 20 mL methanol to produce choline warfarinate as a viscous yellow liquid (5.7 g, 93%).

$^1$H NMR (300 MHz, Methanol-$d_4$) δ=7.96 (dd, J=8.0, 1.9 Hz, 1H), 7.49-7.36 (m, 3H), 7.16 (q, J=7.4 Hz, 4H), 7.05 (t, J=7.4 Hz, 1H), 5.06 (t, J=7.7 Hz, 1H), 3.96 (dq, J=7.7, 2.7 Hz, 2H), 3.47-3.41 (m, 4H), 3.16 (s, 9H), 2.15 (s, 3H). $^{13}$C NMR (101 MHz, Methanol-$d_4$) δ 212.78, 167.50, 154.30, 146.10, 130.65, 128.28, 128.01, 125.63, 125.23, 123.44, 123.02, 116.17, 103.15, 68.41, 68.38, 68.35, 56.41, 54.04, 54.00, 53.95, 49.00, 48.79, 48.57, 48.15, 47.94, 47.73, 47.04, 36.67, 29.35. $FTIR_{vmax}$ ($cm^{-1}$): 3081, 3057, 3028, 1703, 1646, 1598, 1514, 1447, 1406, 1352, 1323, 1272, 1223, 1204, 1154, 1087, 1028, 1004, 953, 896, 865, 833, 759, 700, 630.

Propranolol Saccharin (Pro Sac) Ionic Liquid

The general procedure was applied to propranolol hydrochloride (3.1284 g, 10.576 mmol, 1 equiv.) in 15 ml methanol and sodium saccharin (2.5507 g, 10.575 mmol, 1 equiv.) in 20 ml methanol to produce propranolol saccharin as a viscous yellow liquid (4.7696 g, 97.5%).

$^1$H NMR (300 MHz, $CD_3OD$): δ=8.27 (1H, dd, J=7.4, 2.0 Hz), 7.82-7.79 (1H, m), 7.78-7.73 (2H, m), 7.69-7.61 (2H, m), 7.51-7.41 (3H, ddd, J=11.7, 8.7, 5.9 Hz), 7.37 (1H, t, J=8.0 Hz), 6.93 (1H, d, J=7.5 Hz), 4.46-4.38 (1H, m), 4.29-4.14 (2H, m), 3.49 (1H, p, J=6.6 Hz), 3.40 (1H, dd, J=12.6, 3.1 Hz), 3.26 (1H, dd, J=12.6, 9.6 Hz), 1.38 (6H, dd, J=6.6, 4.0 Hz). $^{13}$C NMR (101 MHz, $CD_3OD$) δ=210.08, 155.40, 145.58, 136.07, 135.02, 133.69, 133.27, 128.56, 127.48, 126.94, 126.82, 126.27, 124.38, 122.78, 121.88, 120.90, 106.16, 71.16, 67.12, 52.06, 48.36, 19.49, 18.92. $FTIR_{vmax}$ ($cm^{-1}$): 3405, 3056, 2987, 2871, 1627, 1579, 1397, 1268, 1143, 947, 771, 680, 602

Example 2

Powders containing the ionic liquids prepared in Example 1 were prepared via spray drying. Spray drying was performed on a Buchi B-290 Mini spray dryer in combination with the B-295 inert loop and two fluid nozzle with a 1.5 mm cap and a 0.7 mm tip. Solutions of the ionic liquid and a polymer in methanol were spray dried using the following process parameters: 667 L $hr^{-1}$ atomising nitrogen flow, 35 $m^3$ $hr^{-1}$ nitrogen drying gas, 6 mL $min^{-1}$ solution feed rate and 80° C. inlet temperature giving an outlet air temperature of 46° C. All solutions were prepared using a polymer concentration of 2.5% (w/v).

The polymers used were ethyl cellulose under the trade name Ethocel Standard 10 Premium (from Dow Wolff Cellulosics GmbH., Bomlitz, Germany), maltodextrin under the trade name Glucidex 6D and Glucidex 19D (from Roquette Frères, Lestrem, France), and a methacrylic acid copolymer under the trade name Eudragit L100 (from Evonik Industries, Essen, Germany).

The composition of the powders prepared are shown in the following table.

| Powder No. | Ionic liquid | Polymer | Weight ratio of ionic liquid to polymer |
|---|---|---|---|
| 1 | BMIm Ibu | Ethocel 10 | 50:50 |
| 2 | BMIm War | Ethocel 10 | 50:50 |
| 3 | Cho Ibu | Ethocel 10 | 50:50 |
| 4 | Cho War | Ethocel 10 | 50:50 |
| 5 | BMIm Ibu | Glucidex 6D | 50:50 |
| 6 | BMIm Ibu | Glucidex 19D | 50:50 |
| 7 | BMIm Ibu | Eudragit L100 | 50:50 |
| 8 | BMIm Ibu | Ethocel 10 | 75:25 |
| 9 | BMIm Ibu | Ethocel 4 | 50:50 |
| 10 | BMIm Ibu | Ethocel 4 | 75:25 |
| 11 | Pro Sac | Ethocel 10 | 50:50 |

The powders 1 to 10 obtained in the table above were characterised.

Fourier Transform-Infrared (FTIR) Spectroscopy

IR spectra for the pure ionic liquids, pure polymers, and powders were obtained using a Spectrum 1 FT-IR Spectrometer (Perkin Elmer, Connecticut, U.S.A) equipped with a Universal Attenuated Total Reflectance and diamond/ZnSe crystal accessory. Each spectrum was scanned in the range of 600-4000 $cm^{-1}$ with a resolution of 1 $cm^{-1}$.

Infrared spectroscopy was used to probe the interactions between the ionic liquid and the polymer in the powders by superimposing the IR spectra for the pure ionic liquids, pure polymers, and powders. Shifts in the spectra at points corresponding to functional groups capable of hydrogen bonding were indicative of hydrogen bonding between the ionic liquid and the polymer, and by extension, miscibility between the ionic liquid and the polymer. On the other hand, in a phase separated system it was expected that little to no shifting of the groups with the potential to form hydrogen bonds would occur. In FIGS. 1 to 4, the dotted reference lines correspond to the wavenumbers of the functional groups where shifting would be expected.

FIG. 1 shows the IR spectrum of Powders 1 and 8. The peak at 1580 $cm^{-1}$ corresponds to C═O stretching in the carboxylate group of the ibuprofen molecule. This is the only distinguishable functional group in the molecule freely available to form hydrogen bonds with the polymer. In Powders 1 and 8 this peak remains at 1580 $cm^{-1}$ and so is not interacting with the ethyl cellulose. This is evidence of a phase separated system.

Figure 2:
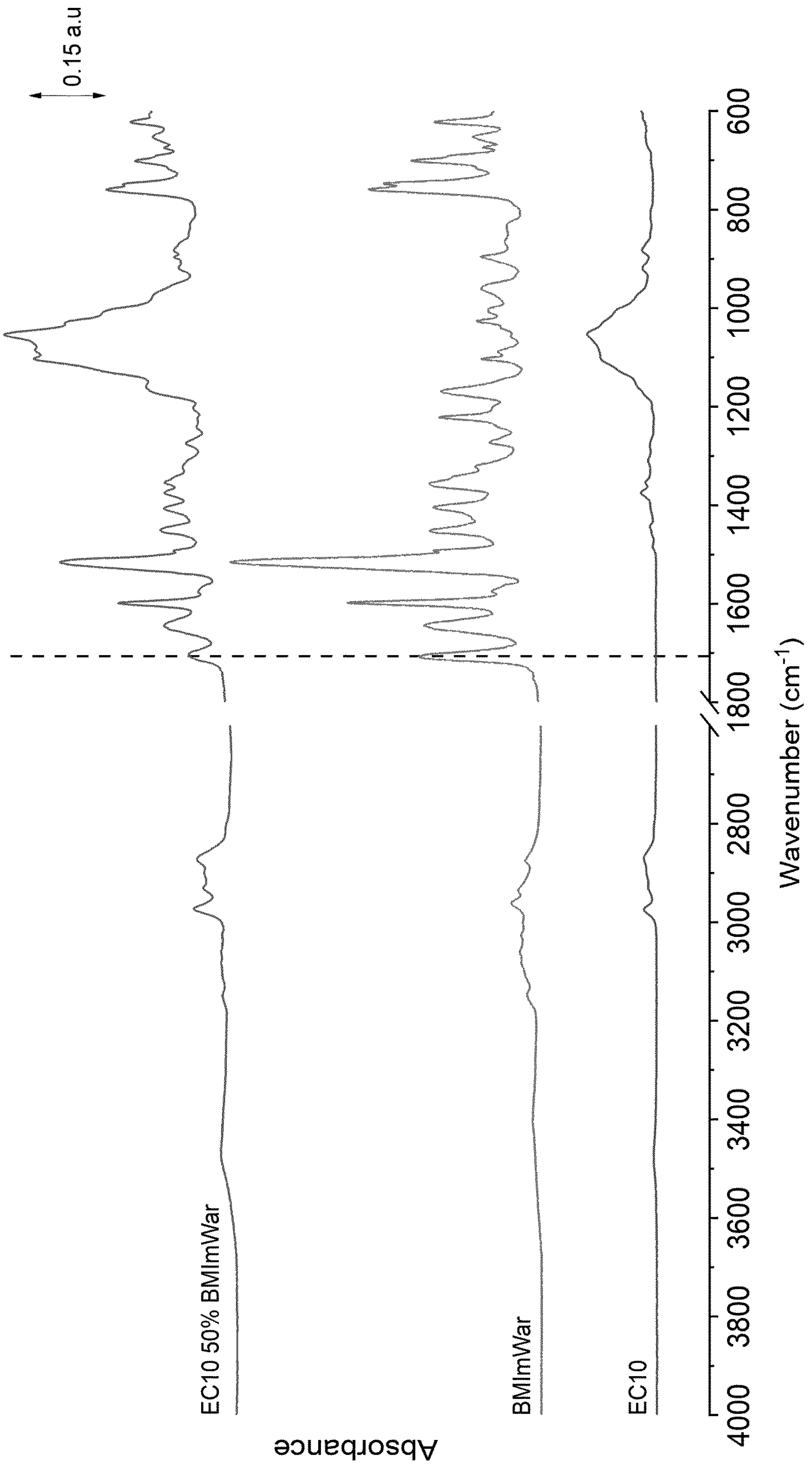
FIG. 2 shows IR spectra of 1-butyl-3-methyl imidazolium warfarinate (BMIm War), Ethocel Standard 10 Premium (EC10), and a spray dried powder comprising 50% w/w BMIm War and 50% w/w EC10.

FIG. 2 shows the IR spectrum of Powder 2. The peak at 1706 $cm^{-1}$ corresponds to C═O stretching in the carbonyl groups of the warfarin molecule. These are the only distinguishable functional groups in the molecule freely available to form hydrogen bonds with the polymer. In Powder 2 this peak remains at 1706 $cm^{-1}$ and so is not interacting with the ethyl cellulose. This is evidence of a phase separated system.

Figure 3:
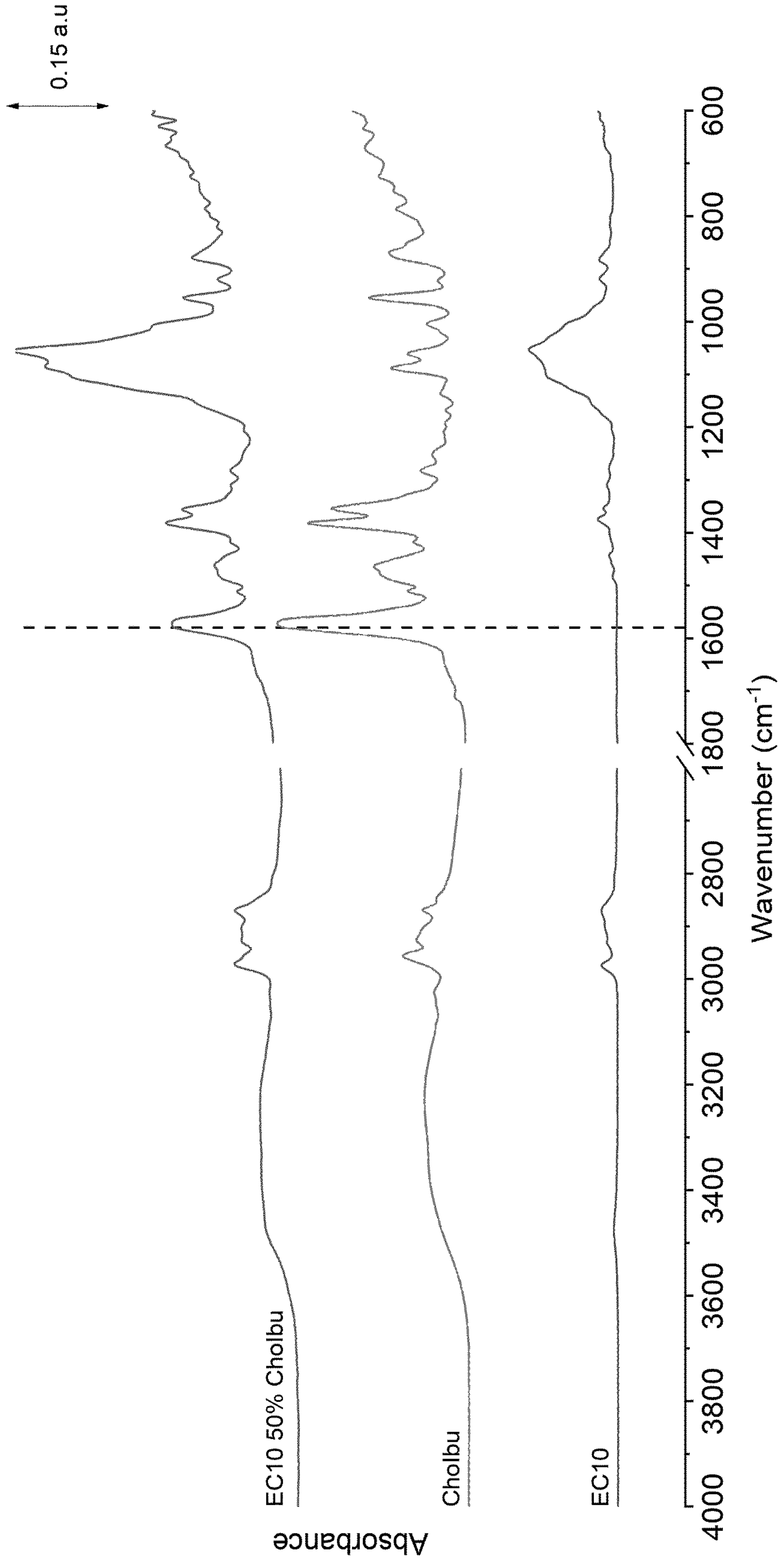
FIG. 3 shows IR spectra of choline ibuprofenate (Cho Ibu), Ethocel Standard 10 Premium (EC10), and a spray dried powder comprising 50% w/w Cho Ibu and 50% w/w EC10.

FIG. 3 shows the IR spectrum of Powder 3. The peak at 1580 $cm^{-1}$ corresponds to C═O stretching in the carboxylate group of the ibuprofen molecule. This is the only distinguishable functional group in the molecule freely available to form hydrogen bonds with the polymer. In Powder 3 this peak remains at 1580 $cm^{-1}$ and so is not interacting with the ethyl cellulose. This is evidence of a phase separated system.

Figure 4:
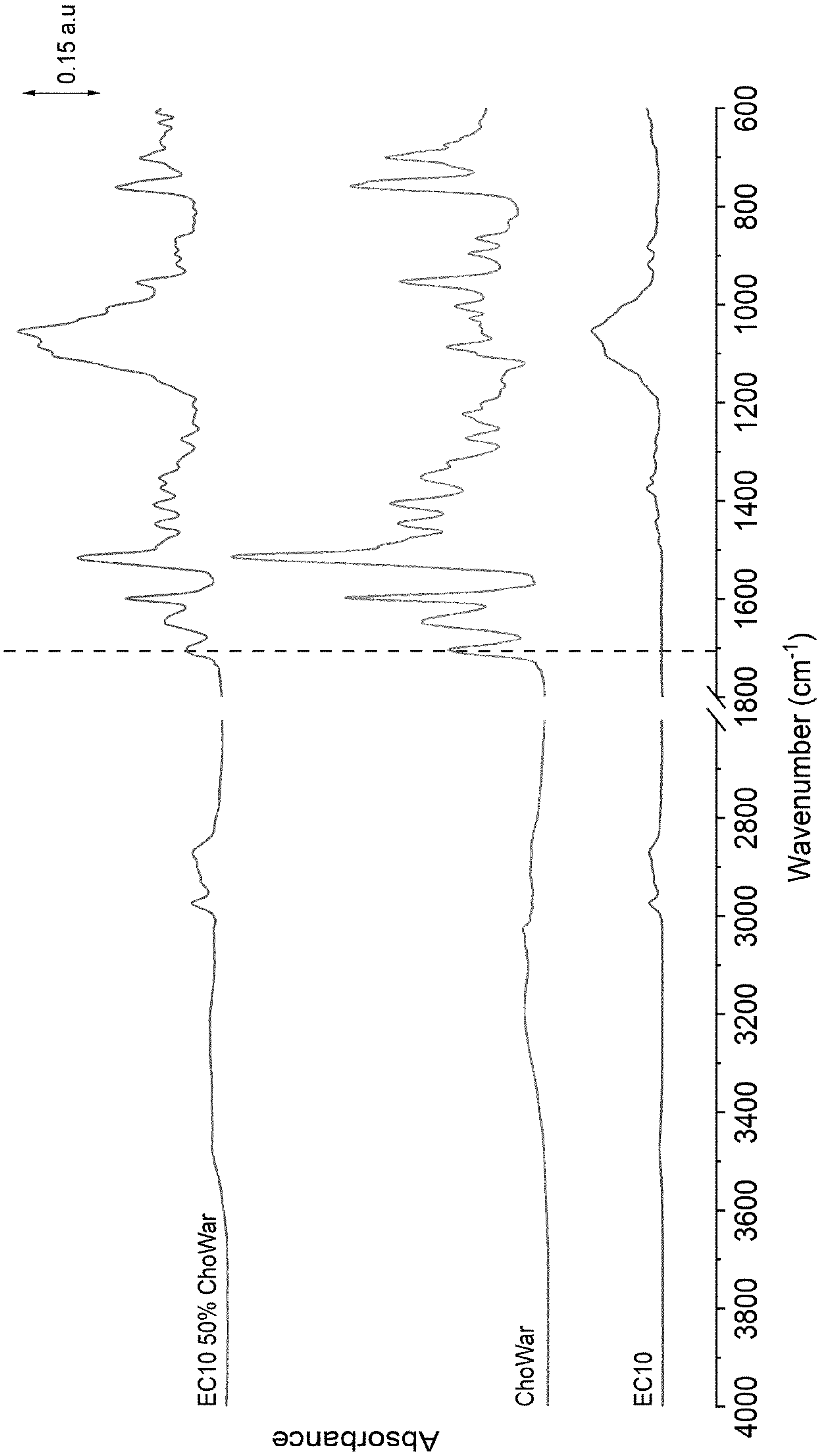
FIG. 4 shows IR spectra of choline warfarinate (Cho War), Ethocel Standard 10 Premium (EC10), and a spray dried powder comprising 50% w/w Cho War and 50% w/w EC10.

FIG. 4 shows the IR spectrum of Powder 4. The peak at 1706 $cm^{-1}$ corresponds to C═O stretching in the carbonyl groups of the warfarin molecule. These are the only distinguishable functional groups in the molecule freely available to form hydrogen bonds with the polymer. In the spray dried product this peak remains at 1706 $cm^{-1}$ and so is not interacting with the ethyl cellulose. This is evidence of a phase separated system.

Figure 24:
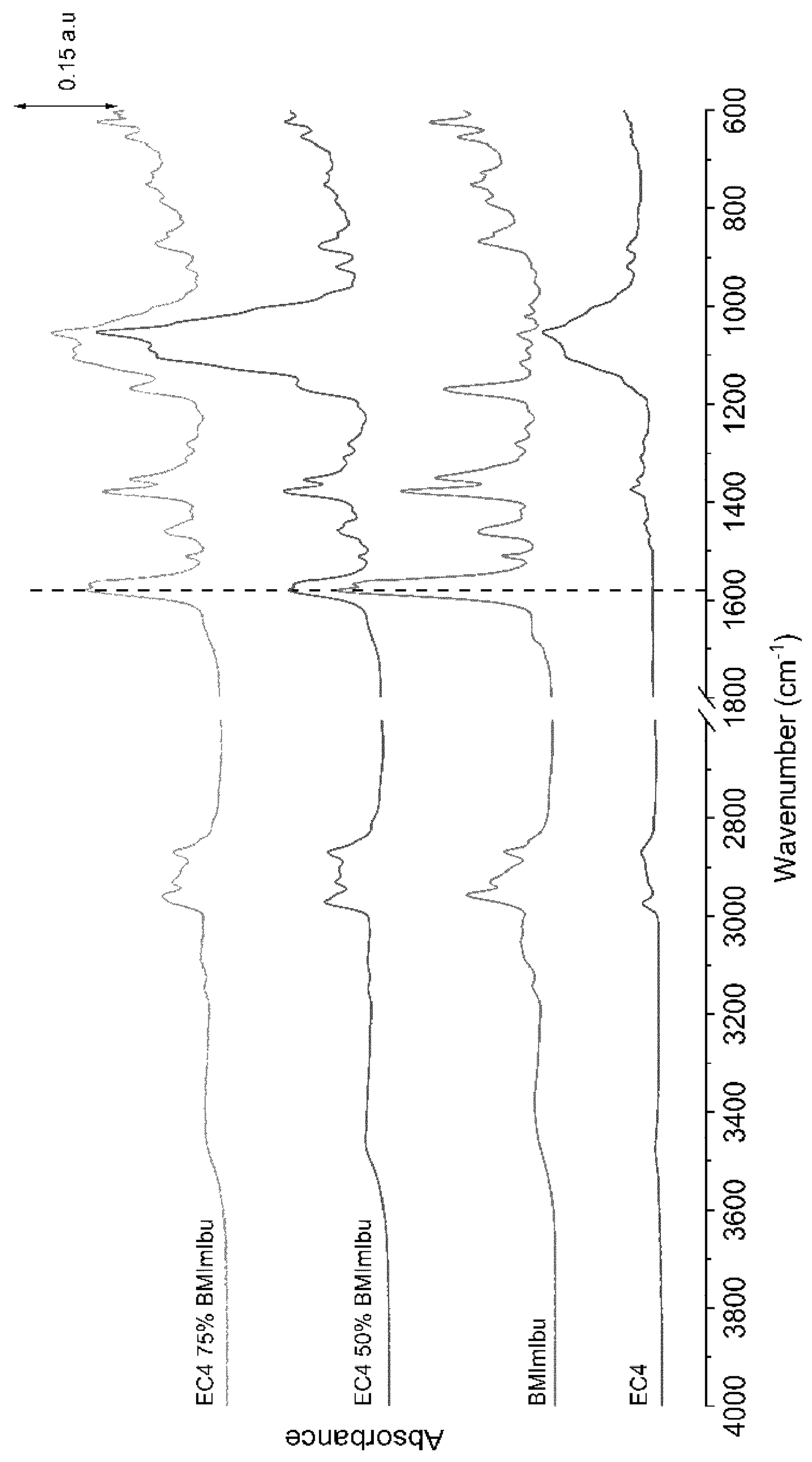
FIG. 24 shows IR spectra of 1-butyl-3-methyl imidazolium ibuprofenate (BMIm Ibu), Ethocel Standard 4 Premium (EC4), a spray dried powder comprising 50% w/w BMIm Ibu and 50% w/w EC4, and a spray dried powder comprising 75% w/w BMIm Ibu and 25% w/w EC4.

FIG. 24 shows the IR spectrum of Powders 9 and 10. The peak at 1580 $cm^{-1}$ corresponds to C═O stretching in the carboxylate group of the ibuprofen molecule. This is the only distinguishable functional group in the molecule freely available to form hydrogen bonds with the polymer. In Powders 9 and 10 this peak remains at 1580 $cm^{-1}$ and so is not interacting with the ethyl cellulose. This is evidence of a phase separated system.

Thermogravimetric Analysis (TGA)

Figure 5:
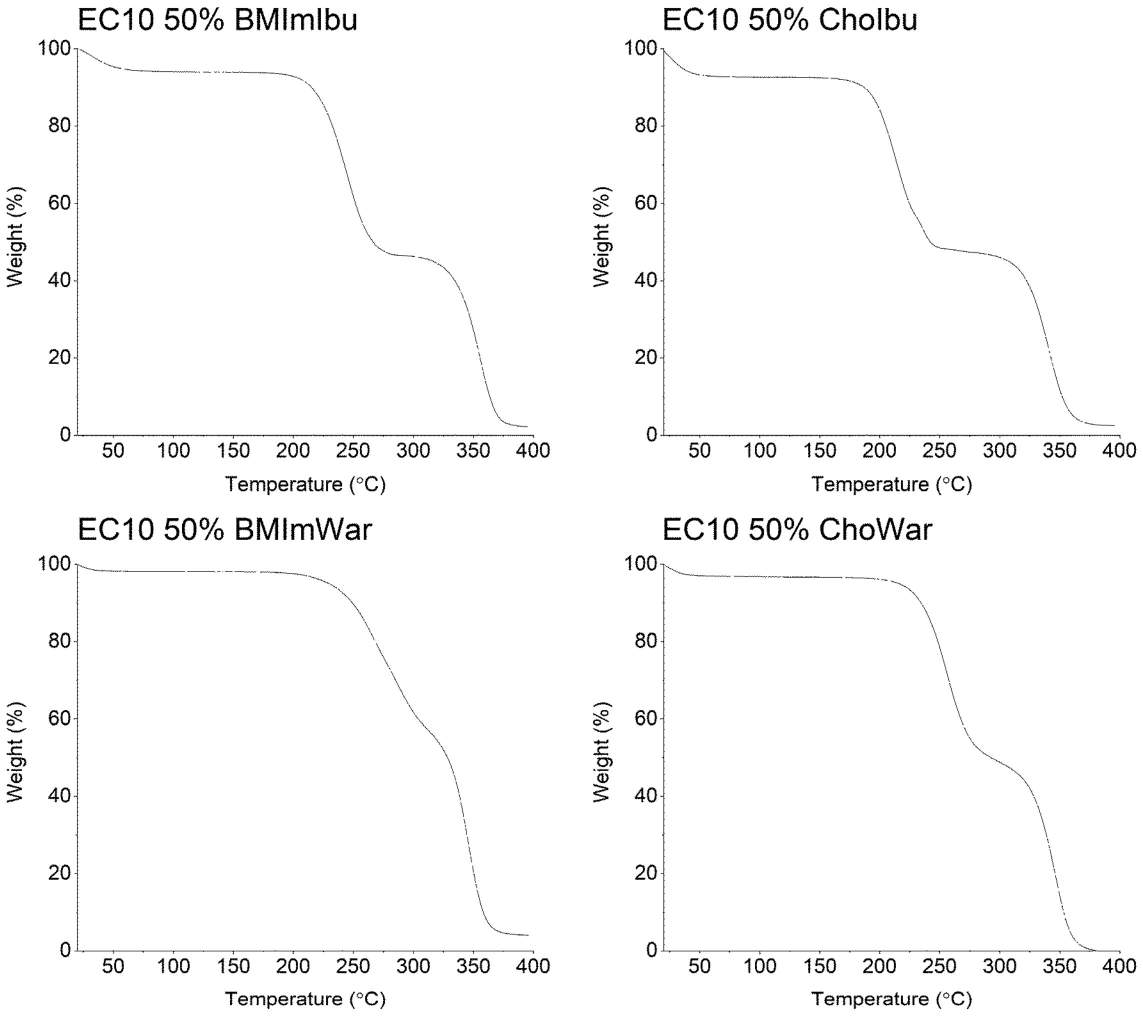
FIG. 5 shows TGA thermograms of spray dried powders comprising 50% w/w Ethocel Standard 10 Premium (EC10) and 50% w/w 1-butyl-3-methyl imidazolium ibuprofenate (BMIm Ibu), 1-butyl-3-methyl imidazolium warfarinate (BMIm War), choline ibuprofenate (Cho Ibu), or choline warfarinate (Cho War).

TGA involved heating samples under an inert atmosphere on a balance and tracking mass loss as a function of temperature. This allowed moisture content and degradation points to be determined and also served as a rough indication of the composition of the material (with the stepwise degradation of the ionic liquid followed by that of the polymer approximately corresponding to the mass fraction of the respective components). TGA was carried out using a QA-50 device (TA instruments, Elstree, United Kingdom). Open aluminium pans holding 5-10 mg of sample were heated at a constant rate of 10° C. $min^{-1}$ under an inert nitrogen atmosphere from 25-400° C. FIG. 5 shows the thermograms of Powders 1 to 4. The moisture content of Powders 1 to 4 was between 3 and 7.5%.

Modulated Differential Scanning Calorimetry (mDSC)

Modulated differential scanning calorimetry (mDSC) was used to determine the physical properties of the pure ionic liquids, pure polymers, and powders based on how they behaved when put through heating and cooling cycles. In addition to solid-liquid state phase transformations, solid-solid state phase transformations (such glass transition and crystallisation) were determined from how the heat flow (y axis) varied as a function of temperature. Ordinarily, a powder having a single ionic liquid-polymer phase was expected to exhibit a single glass transition at a point between that of the pure components. The presence of two glass transitions was strong evidence of a phase separated system.

All mDSC measurements were performed on a QA-200 TA instrument (TA instruments, Elstree, United Kingdom) calorimeter using nitrogen as the purge gas. Samples of Powders 1 to 7 (3-5 mg) were placed in closed standard aluminium pans, while a similar mass of the pure ionic liquid was placed in a sealed hermetic pan with one pin hole (n=3). All samples were run in triplicate and the machine was calibrated using indium as a standard. As the presence of trace amount of water in a sample can cause a significant depression of the $T_g$ of materials, a drying cycle was included as part of the mDSC method. The method proceeded as follows: samples were equilibrated at 20° C. and held isothermally for 5 min. The temperature was then ramped to 110° C. at a rate of 5° C. $min^{-1}$ with a modulation of 0.8° C. every 60 seconds and held there for 10 min in order to remove any residual moisture. The modulation was maintained for the remainder of the experiment. The sample was then cooled to −50° C. at 5° C. $min^{-1}$ and again held there for 10 min before finally being ramped to 190° C. at 5° C. $min^{-1}$.

mDSC measurements of the pure polymers were obtained as described above, with the polymers being placed in standard aluminium pans.

FIGS. 6 to 12 show reversible heat flow mDSC thermograms of Powders 1 to 8 compared to the corresponding pure ionic liquid and pure polymer for the second heating cycle of the above described method. The exotherm is in the upward direction, and glass transitions are indicated by arrows.

Figure 6:
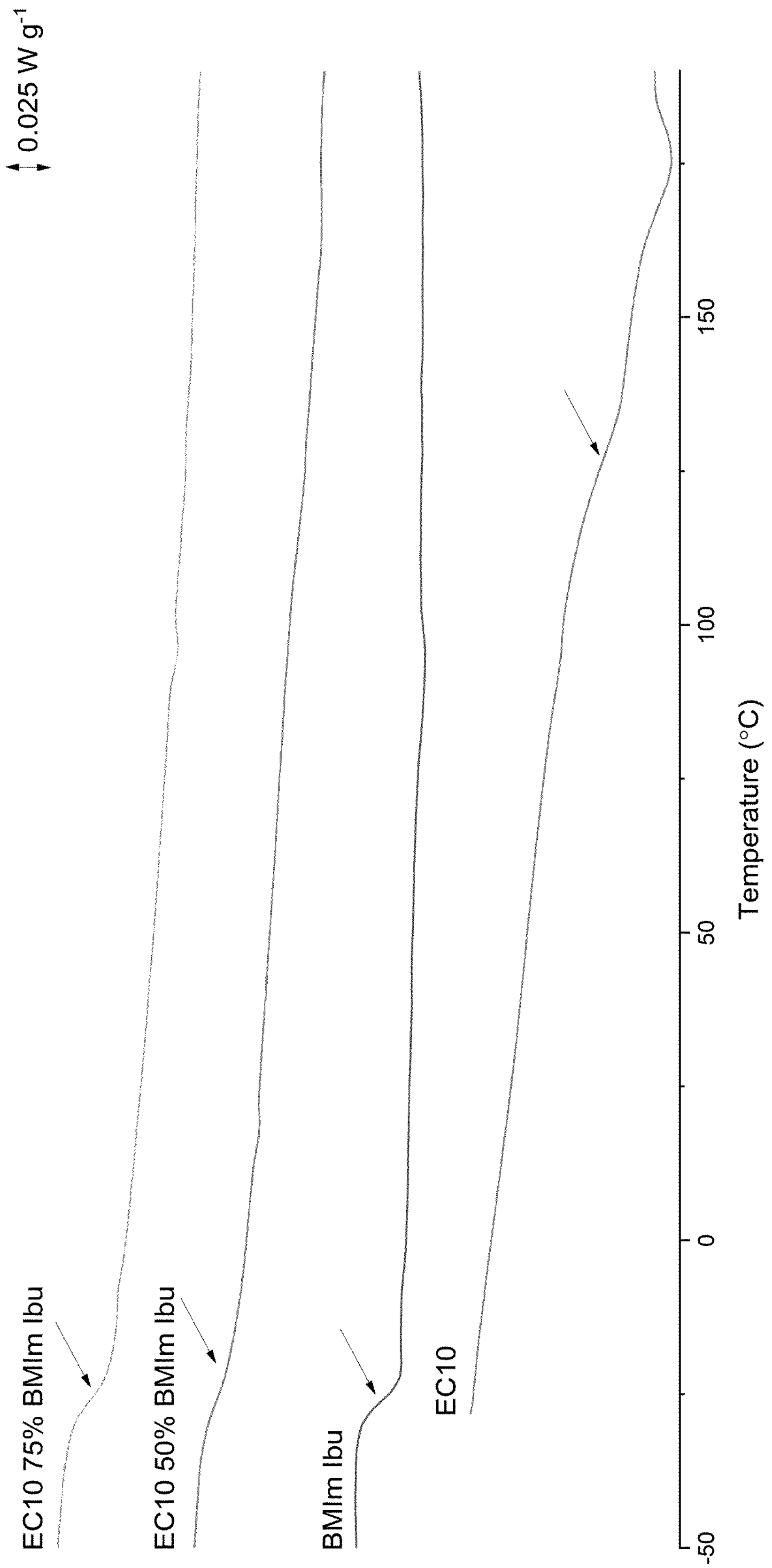
FIG. 6 shows reversible heat flow mDSC thermograms of 1-butyl-3-methyl imidazolium ibuprofenate (BMIm Ibu), Ethocel Standard 10 Premium (EC10), a spray dried powder comprising 50% w/w BMIm Ibu and 50% w/w EC10, and a spray dried powder comprising 75% w/w BMIm Ibu and 25% w/w EC10 for the second heating cycle. The exotherm is in the upward direction.

FIG. 6 shows the mDSC thermogram of Powders 1 and 8. One $T_g$ is present at −25.77° C. for Powder 1 and one $T_g$ is present at −26.38° C. for Powder 8. However, as the single $T_g$s are close to that of the pure ionic liquid (BMIm Ibu), rather than in between the $T_g$ of the ionic liquid and the polymer, they are indicative of a phase separated system. The absence of a second $T_g$, which would normally be indicative of a phase separated system, is explained by the BMIm Ibu initially being phase separated from the polymer and then proceeding to solvate it upon heating. Since the polymer is in a liquid state before its $T_g$ is reached, the $T_g$ is not observed.

Figure 7:
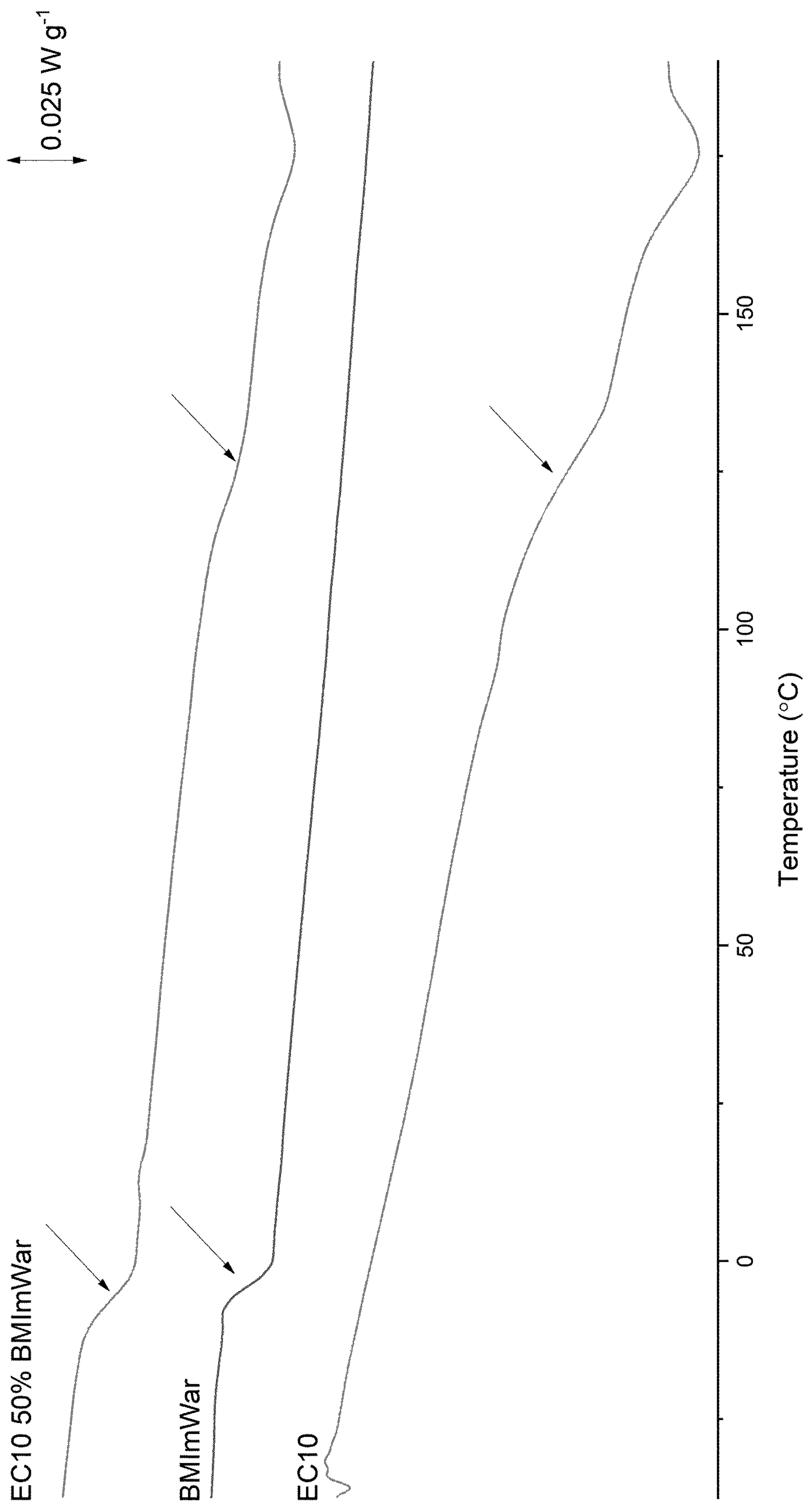
FIG. 7 shows reversible heat flow mDSC thermograms of 1-butyl-3-methyl imidazolium warfarinate (BMIm War), Ethocel Standard 10 Premium (EC10), and a spray dried powder comprising 50% w/w BMIm War and 50% w/w EC10 for the second heating cycle. The exotherm is in the upward direction.

FIG. 7 shows the mDSC thermogram of Powder 2. Two $T_g$s are present at −5.50 and 119.66° C. corresponding to BMIm War and ethyl cellulose, respectively. This is strong evidence of a phase separated system.

Figure 8:
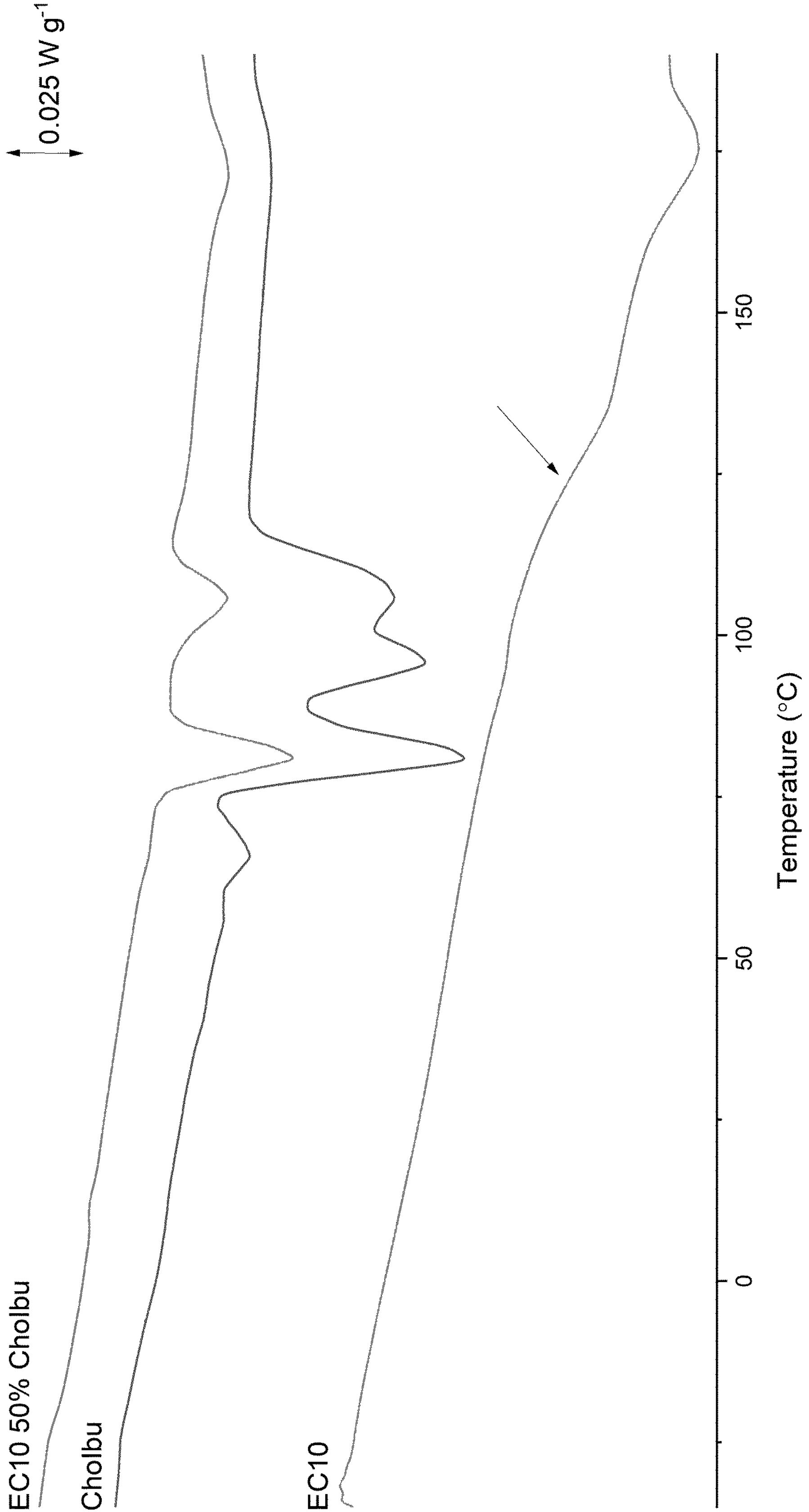
FIG. 8 shows reversible heat flow mDSC thermograms of choline ibuprofenate (Cho Ibu), Ethocel Standard 10 Premium (EC10), and a spray dried powder comprising 50% w/w Cho Ibu and 50% w/w EC10 for the second heating cycle. The exotherm is in the upward direction.

FIG. 8 shows the mDSC thermogram of Powder 3. The sharp troughs at 81.00 and 105.76° C. indicate melting points. As a single phase system would not typically exhibit melting points, this is evidence of a phase separated system.

Figure 9:
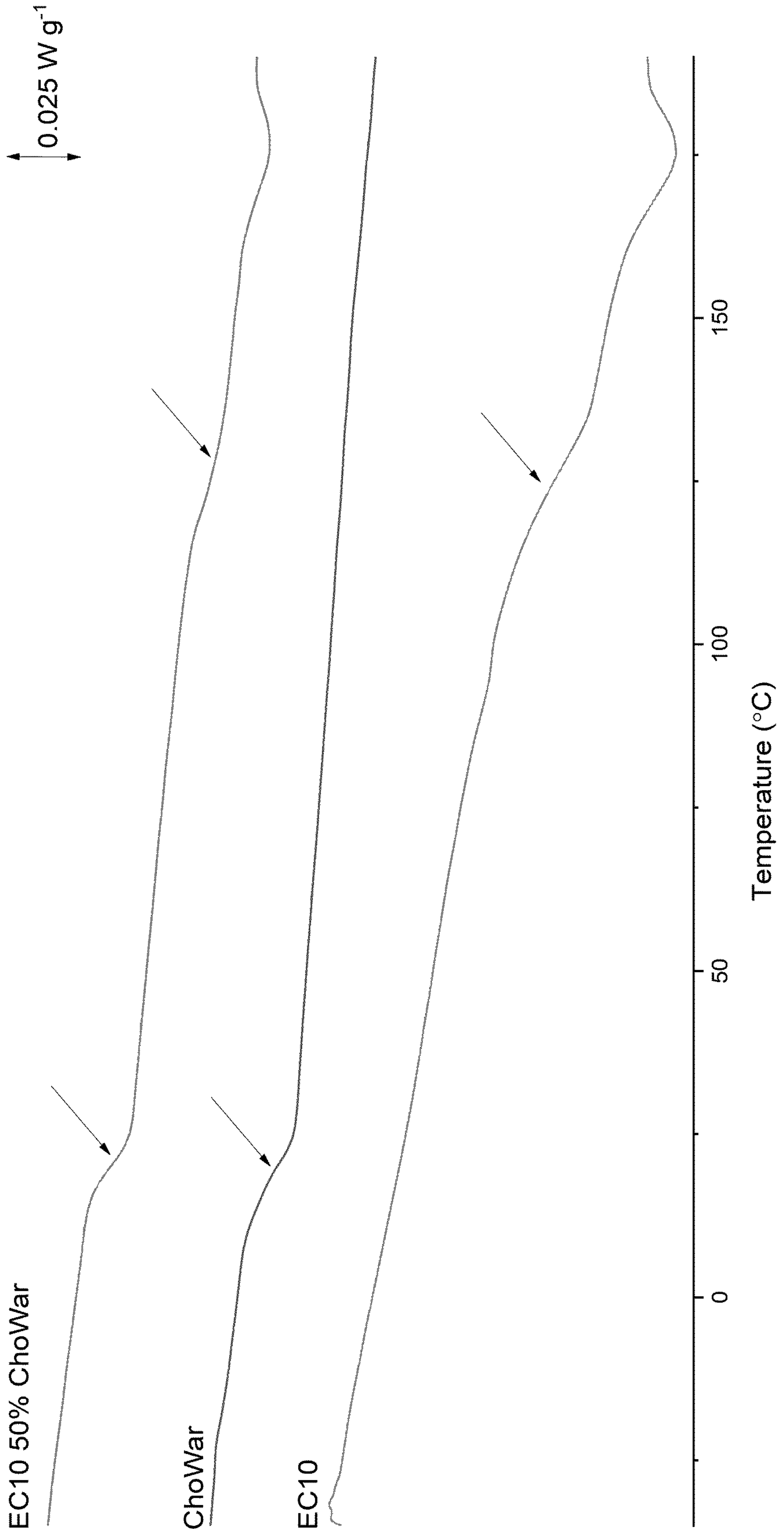
FIG. 9 shows reversible heat flow mDSC thermograms of choline warfarinate (Cho War), Ethocel Standard 10 Premium (EC10), and a spray dried powder comprising 50% w/w Cho War and 50% w/w EC10 for the second heating cycle. The exotherm is in the upward direction.

FIG. 9 shows the mDSC thermogram of Powder 4. Two $T_g$s are present at 20.33 and 119.91° C. corresponding to ChoWar and ethyl cellulose, respectively. This is strong evidence of a phase separated system.

Figure 10:
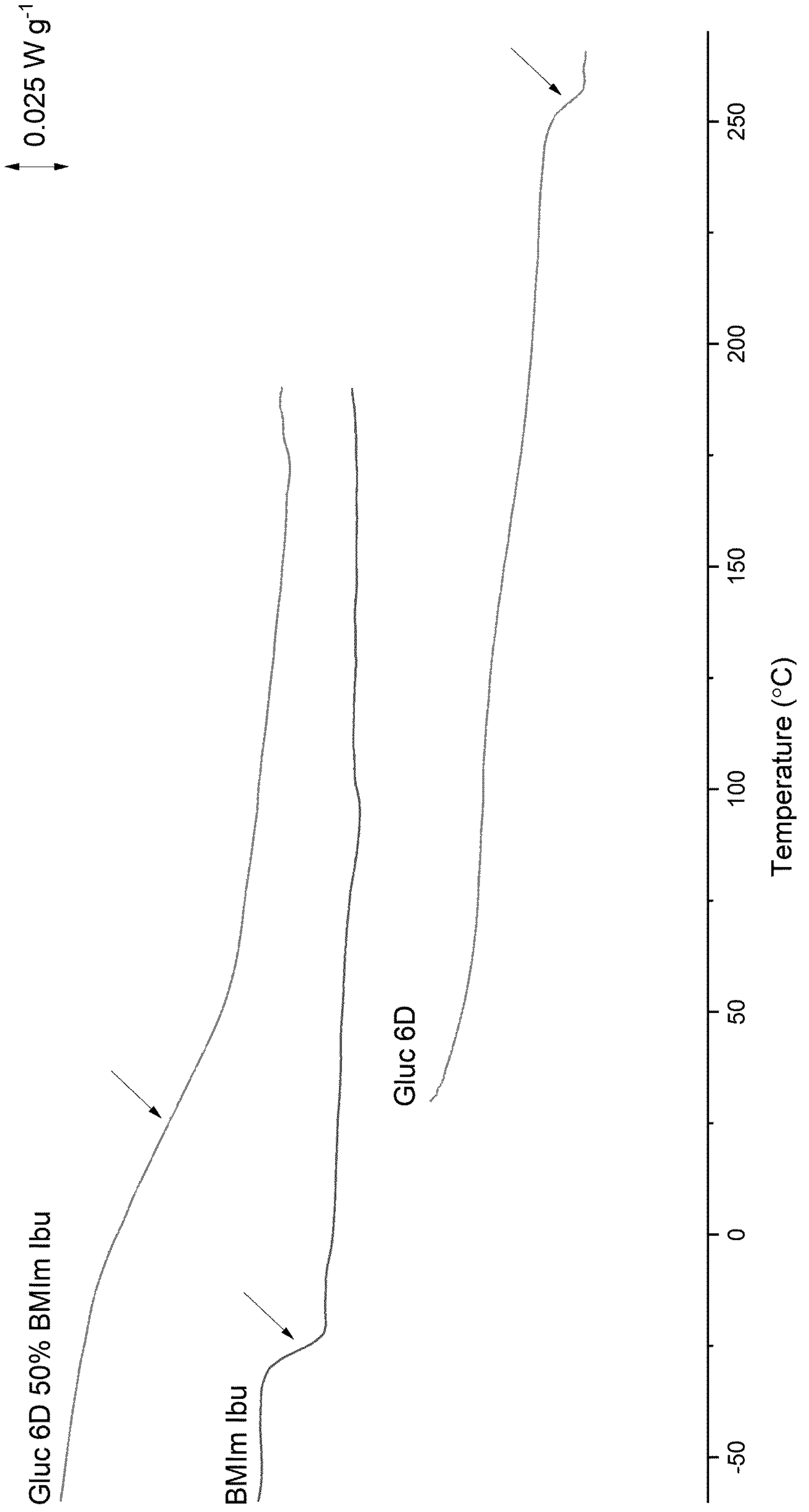
FIG. 10 shows reversible heat flow mDSC thermograms of 1-butyl-3-methyl imidazolium ibuprofenate (BMIm Ibu), Glucidex 6D (Gluc 6D), and a spray dried powder comprising 50% w/w BMIm Ibu and 50% w/w Gluc 6D for the second heating cycle. The exotherm is in the upward direction.

FIG. 10 shows the mDSC thermogram of Powder 5. A single $T_g$ is present at 35.90° C. This lies in between the $T_g$s of the pure BMIm Ibu and Glucidex 6D and is strong evidence of a single phase system.

Figure 11:
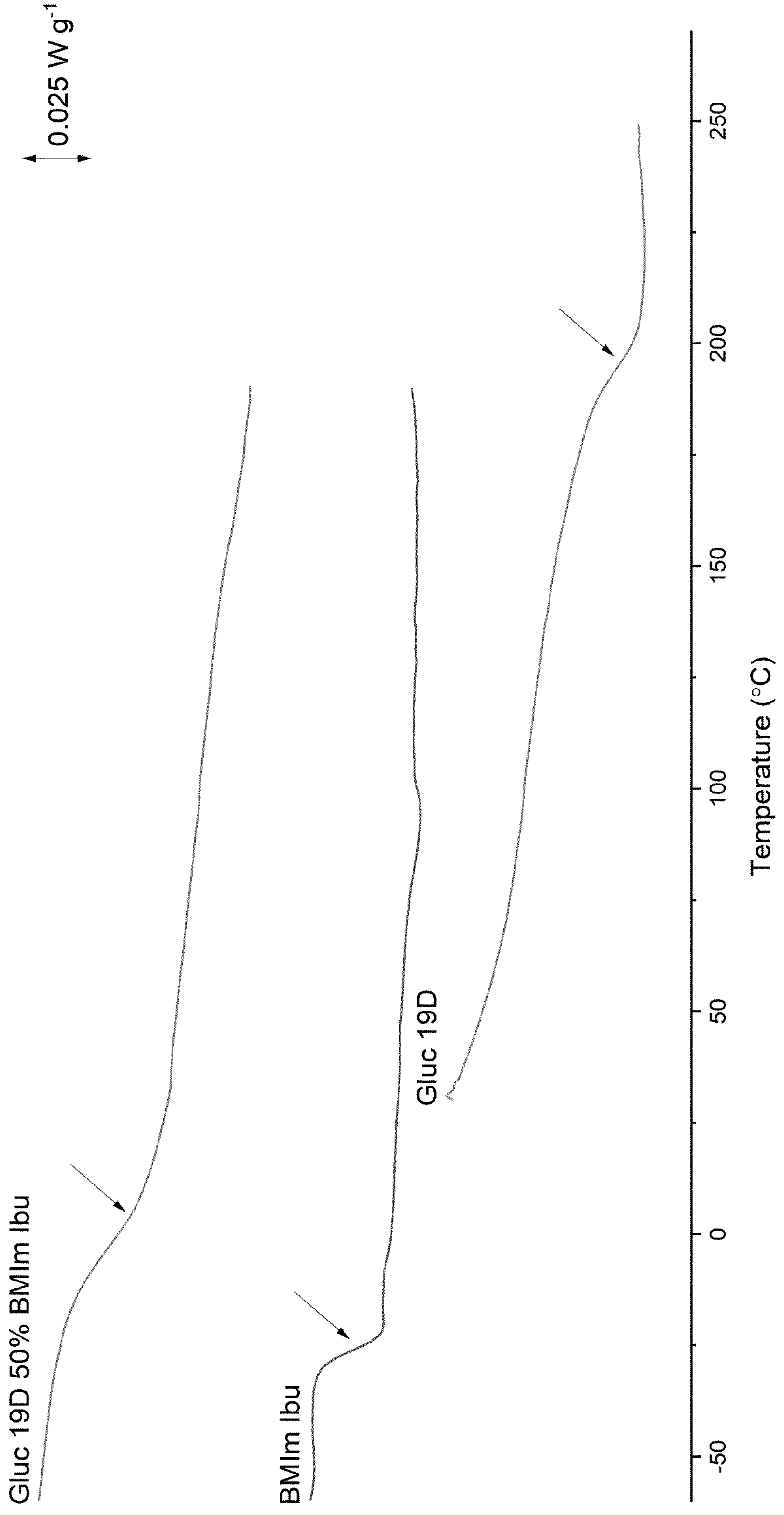
FIG. 11 shows reversible heat flow mDSC thermograms of 1-butyl-3-methyl imidazolium ibuprofenate (BMIm Ibu), Glucidex 19D (Gluc 19D), and a spray dried powder comprising 50% w/w BMIm Ibu and 50% w/w Gluc 19D for the second heating cycle. The exotherm is in the upward direction.

FIG. 11 shows the mDSC thermogram of Powder 6. A single $T_g$ is present at 4.16° C. This lies in between the $T_g$s of the pure BMIm Ibu and Glucidex 19D and is strong evidence of a single phase system.

Figure 12:
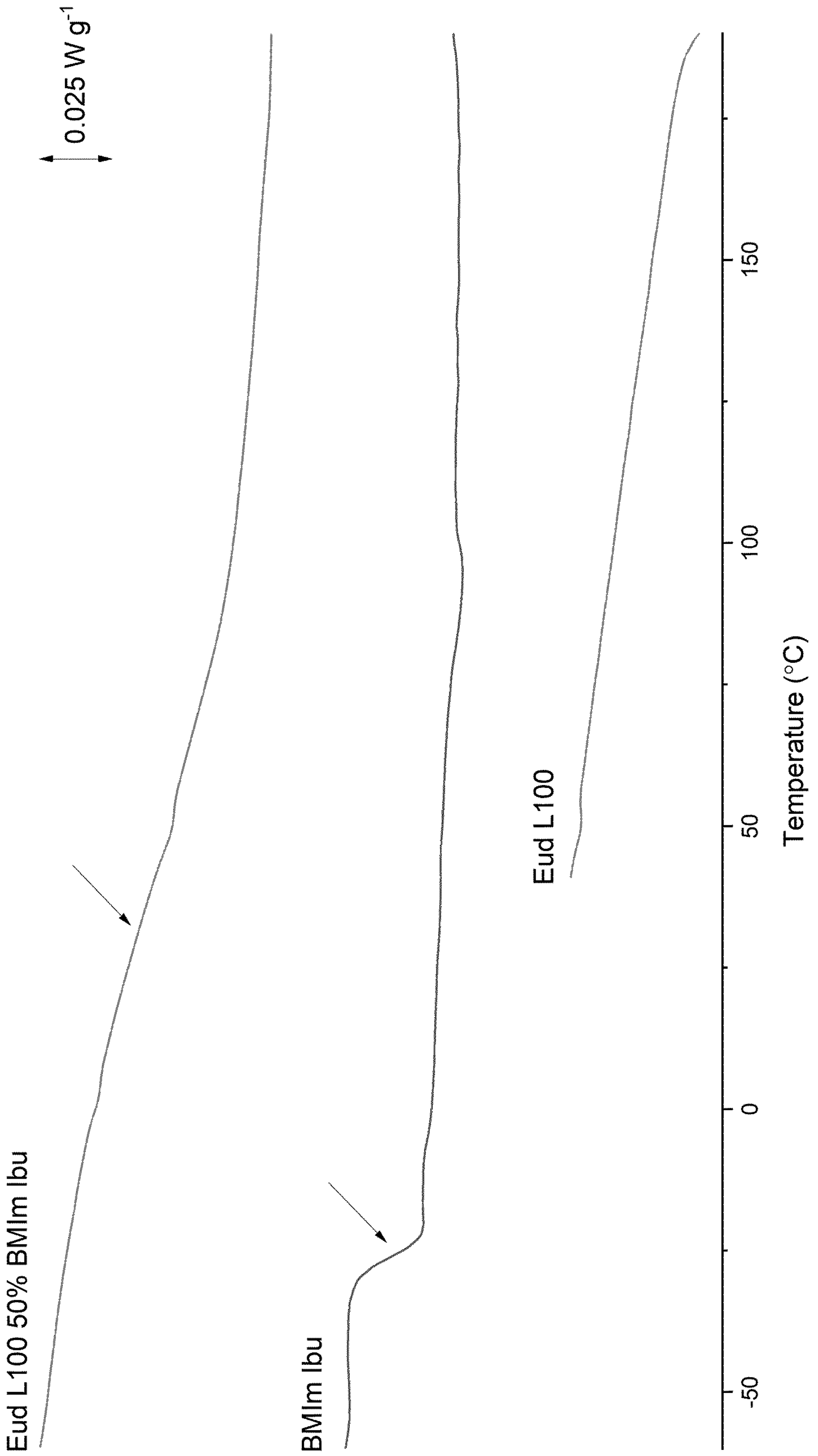
FIG. 12 shows reversible heat flow mDSC thermograms of 1-butyl-3-methyl imidazolium ibuprofenate (BMIm Ibu), Eudragit L100 (Eud L100), and a spray dried powder comprising 50% w/w BMIm Ibu and 50% w/w Eud L100 for the second heating cycle. The exotherm is in the upward direction.
Figure 13:
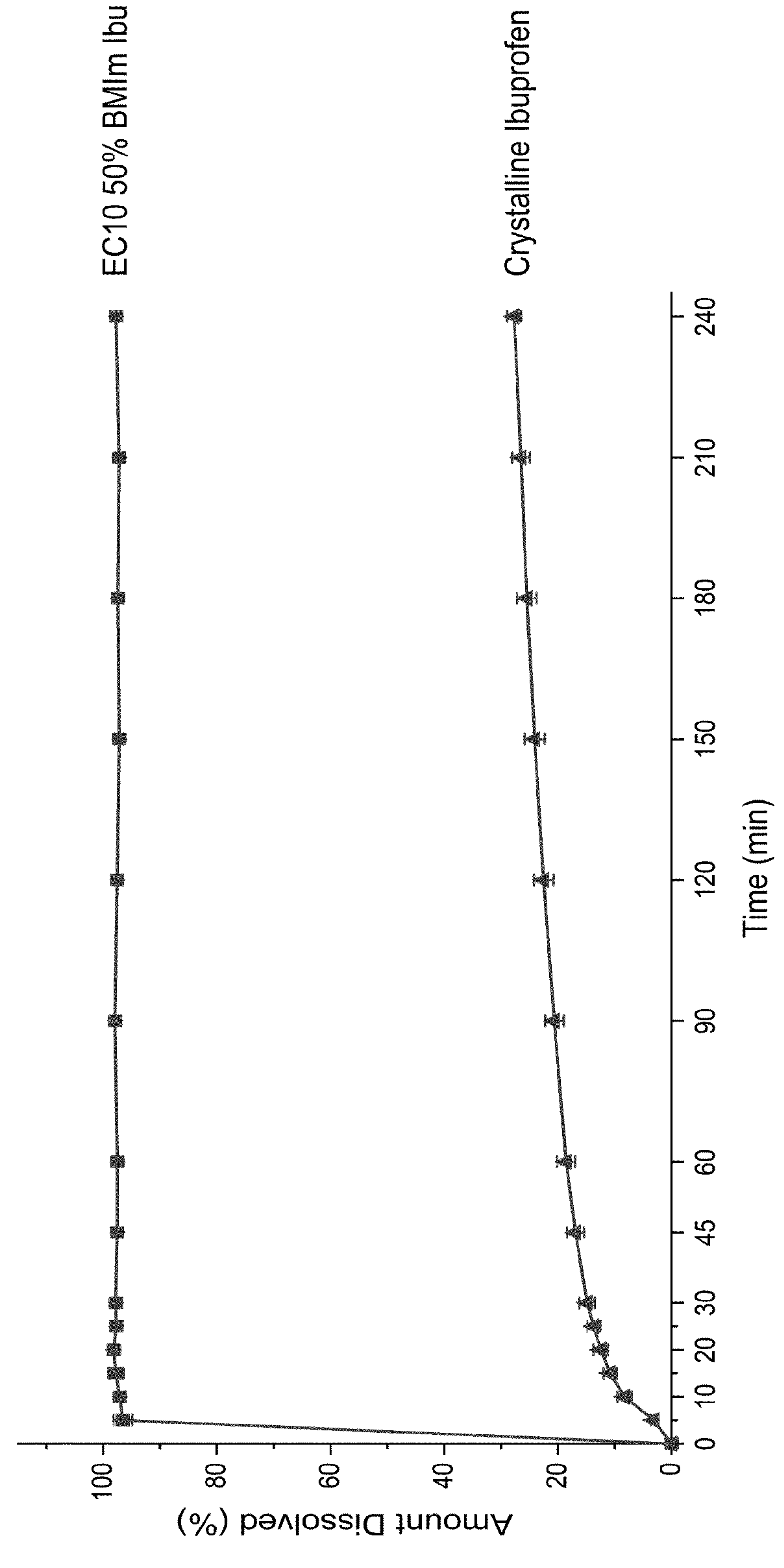
FIG. 13 shows the dissolution profile over time of a spray dried powder comprising 50% w/w BMIm Ibu and 50% w/w EC10 in deionised water compared to crystalline ibuprofen.
Figure 14:
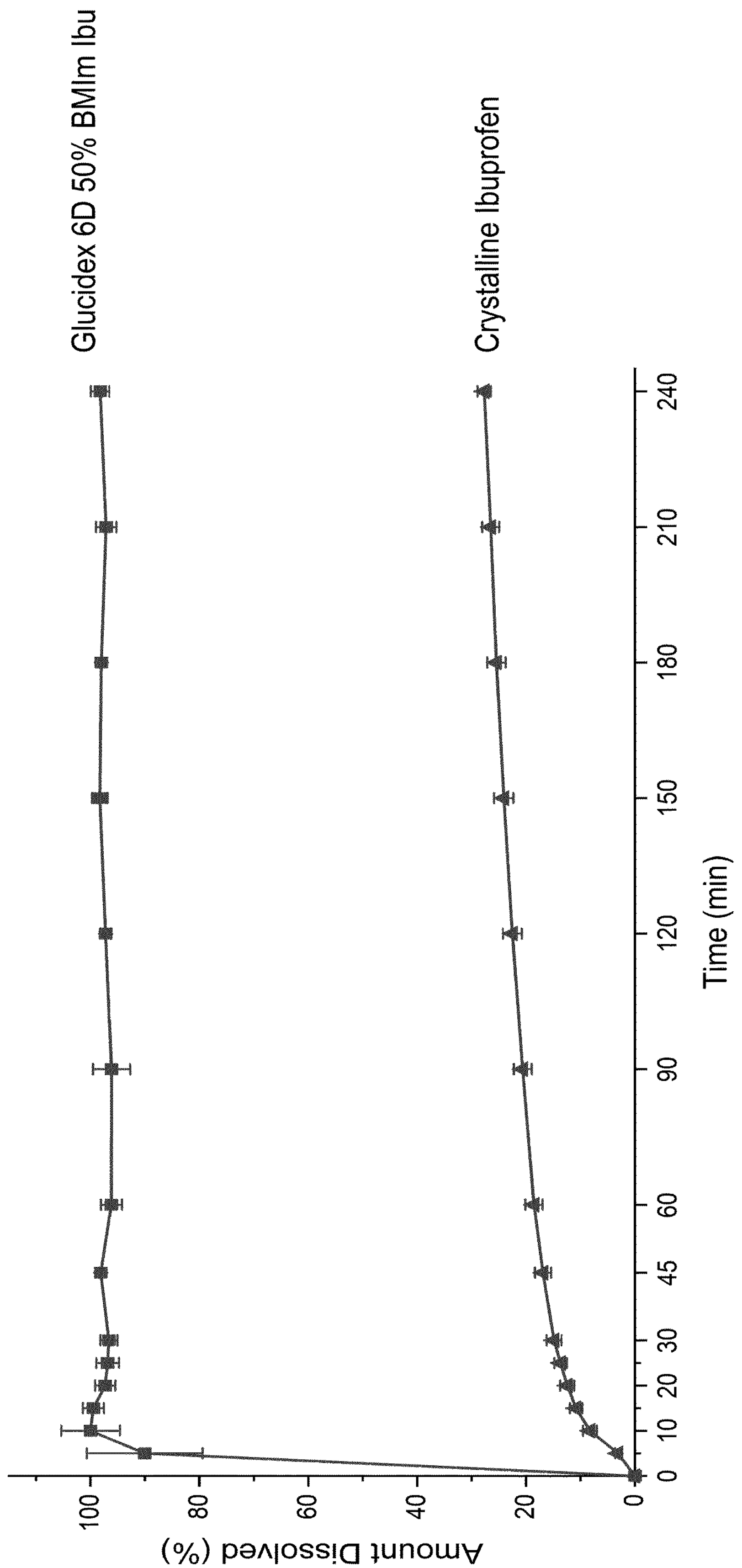
FIG. 14 shows the dissolution profile over time of a spray dried powder comprising 50% w/w BMIm Ibu and 50% w/w Gluc 6D in deionised water compared to crystalline ibuprofen.
Figure 15:
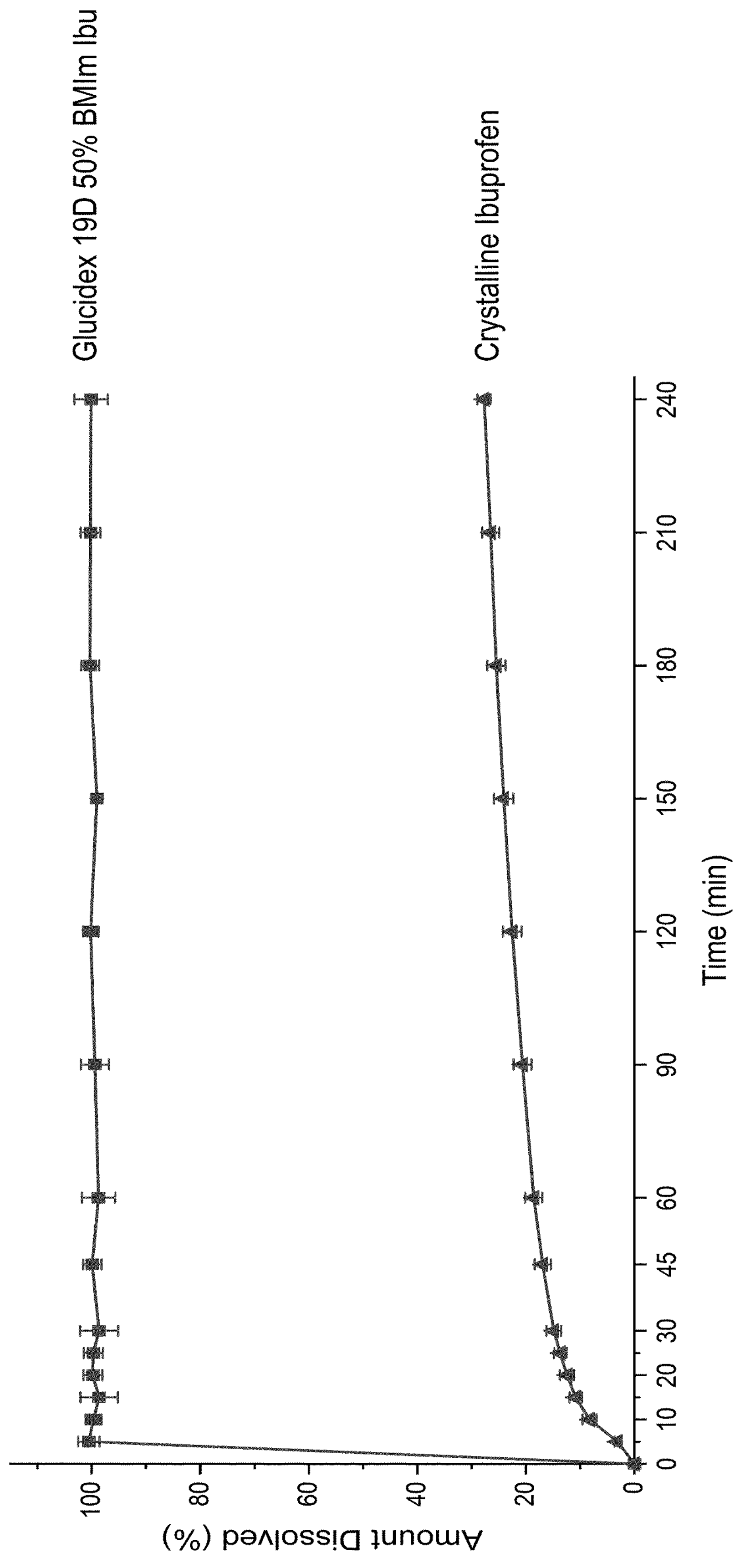
FIG. 15 shows the dissolution profile over time of a spray dried powder comprising 50% w/w BMIm Ibu and 50% w/w Gluc 19D in deionised water compared to crystalline ibuprofen.
Figure 16:
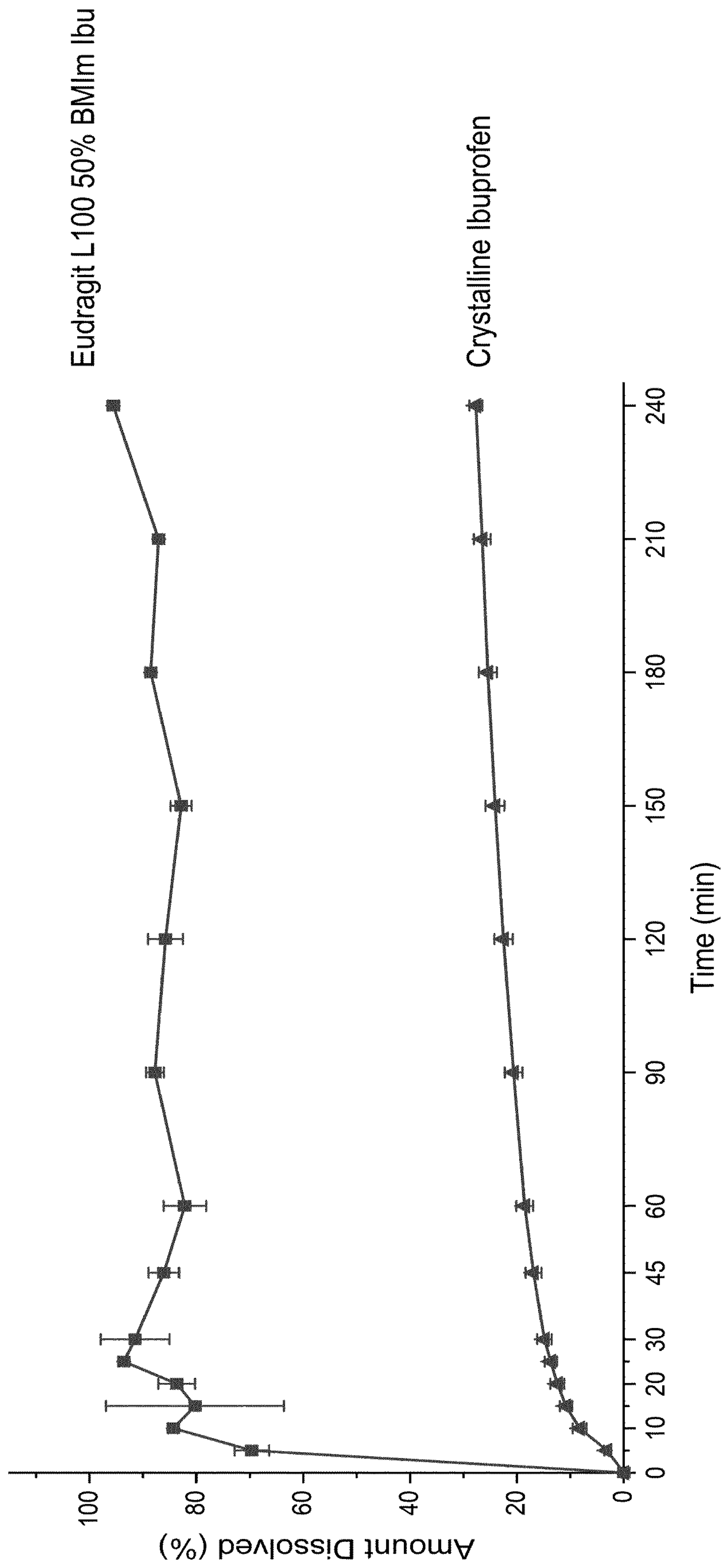
FIG. 16 shows the dissolution profile over time of a spray dried powder comprising 50% w/w BMIm Ibu and 50% w/w Eud L100 in deionised water compared to crystalline ibuprofen.
Figure 17:
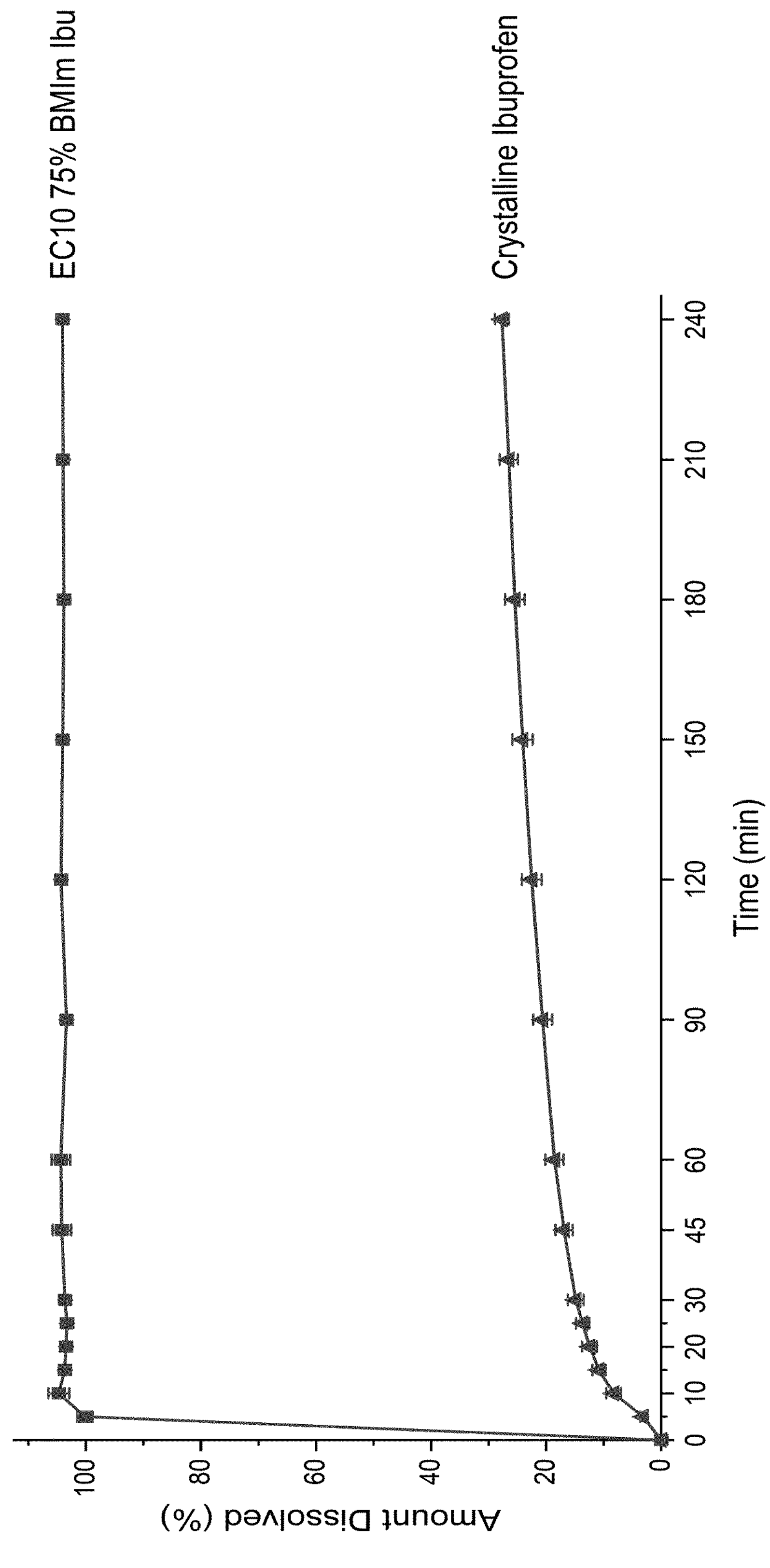
FIG. 17 shows the dissolution profile over time of a spray dried powder comprising 75% w/w BMIm Ibu and 25% w/w EC10 in deionised water compared to crystalline ibuprofen.

FIG. 12 shows the mDSC thermogram of Powder 7. A single faint $T_g$ is present at 23.68° C. This lies in between the $T_g$s of the pure BMIm Ibu and Eudragit L100 and is strong evidence of a single phase system.

Figure 25:
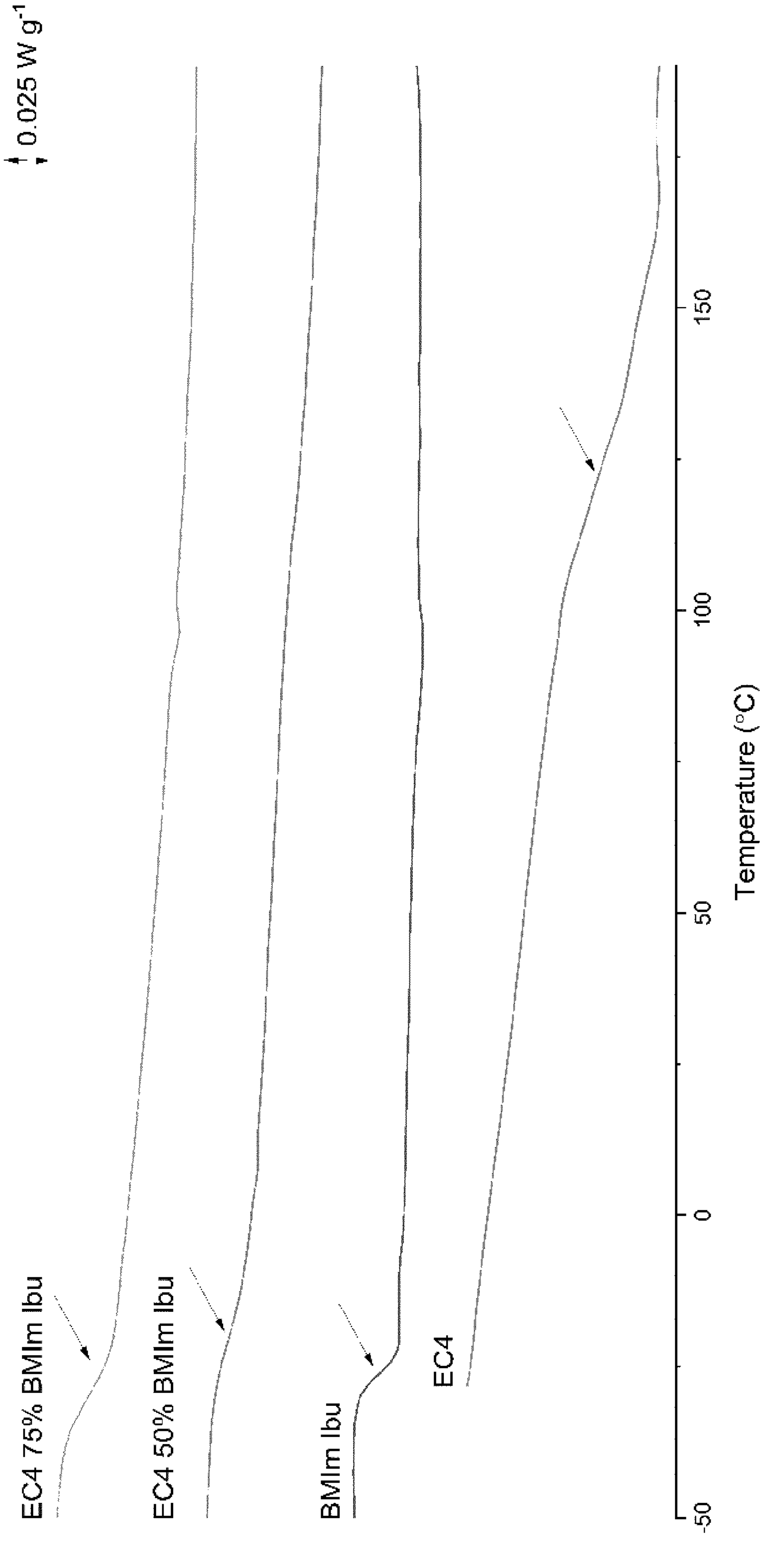
FIG. 25 shows reversible heat flow mDSC thermograms of BMIm Ibu, Ethocel Standard 4 Premium (EC4), a spray dried powder comprising 50% w/w BMIm Ibu and 50% w/w EC4, and a spray dried powder comprising 75% w/w BMIm Ibu and 25% w/w EC4 for the second heating cycle. The exotherm is in the upward direction.

FIG. 25 shows reversible heat flow mDSC thermograms of Powders 9 and 10 compared to the corresponding pure ionic liquid and pure polymer for the second heating cycle of the above described method. The exotherm is in the upward direction, and glass transitions are indicated by arrows.

Dissolution

Dissolution studies were performed using a USP Apparatus 2 with a Sotax AT7 dissolution bath (Carl Stuart Limited, Dublin, Ireland). The mass of powder corresponding to the equivalent of 200 mg of ibuprofenate ion (equivalent to one dose) was added to 900 ml of dissolution media equilibrated at 37° C. stirred at 50 rpm. Samples were taken and replaced with fresh media every 5 min for the first 30 min, then at 45 min, 60 min and then every 30 min for the remainder of the experiment. The first 2 ml of each 5 ml sample was filtered and discarded before the remaining sample was filtered through a 0.45 μm nylon filter into a HPLC vial. All experiments were carried out in triplicate. A sample of the powder was assayed by completely dissolving it in methanol (n=3) and finding the ionic liquid content by HPLC.

The dissolution of powders 1 and 5 to 8 in deionised water over a period of four hours was studied. As shown in FIGS. 13 to 17, after 10 minutes and until the end of the four hours, the level of dissolution of the ionic liquid in Powders 1 and 5 to 8 was close to 100%.

Figure 26:
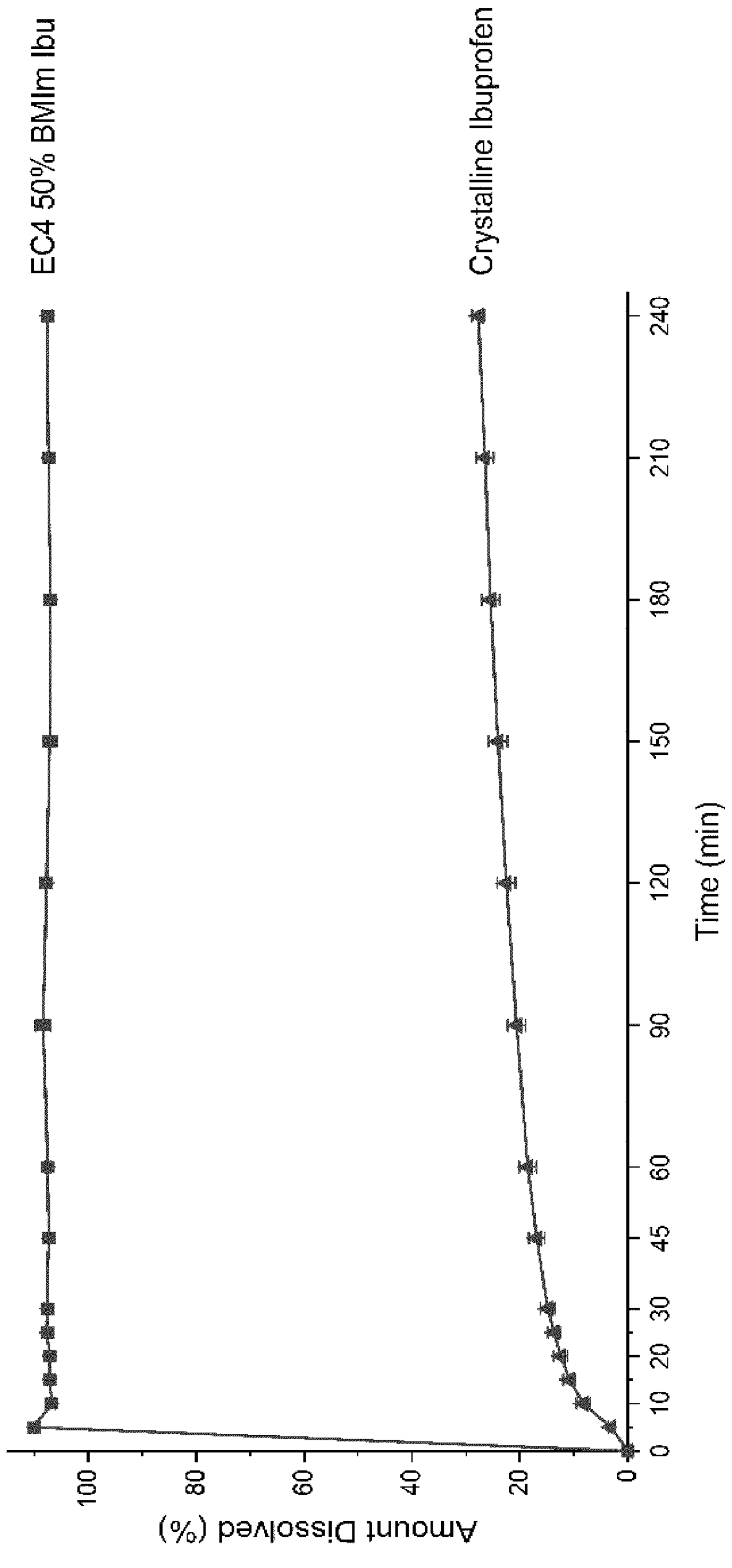
FIG. 26 shows the dissolution profile over time of a spray dried powder comprising 50% w/w BMIm Ibu and 50% w/w EC4 in deionised water compared to crystalline ibuprofen.
Figure 27:
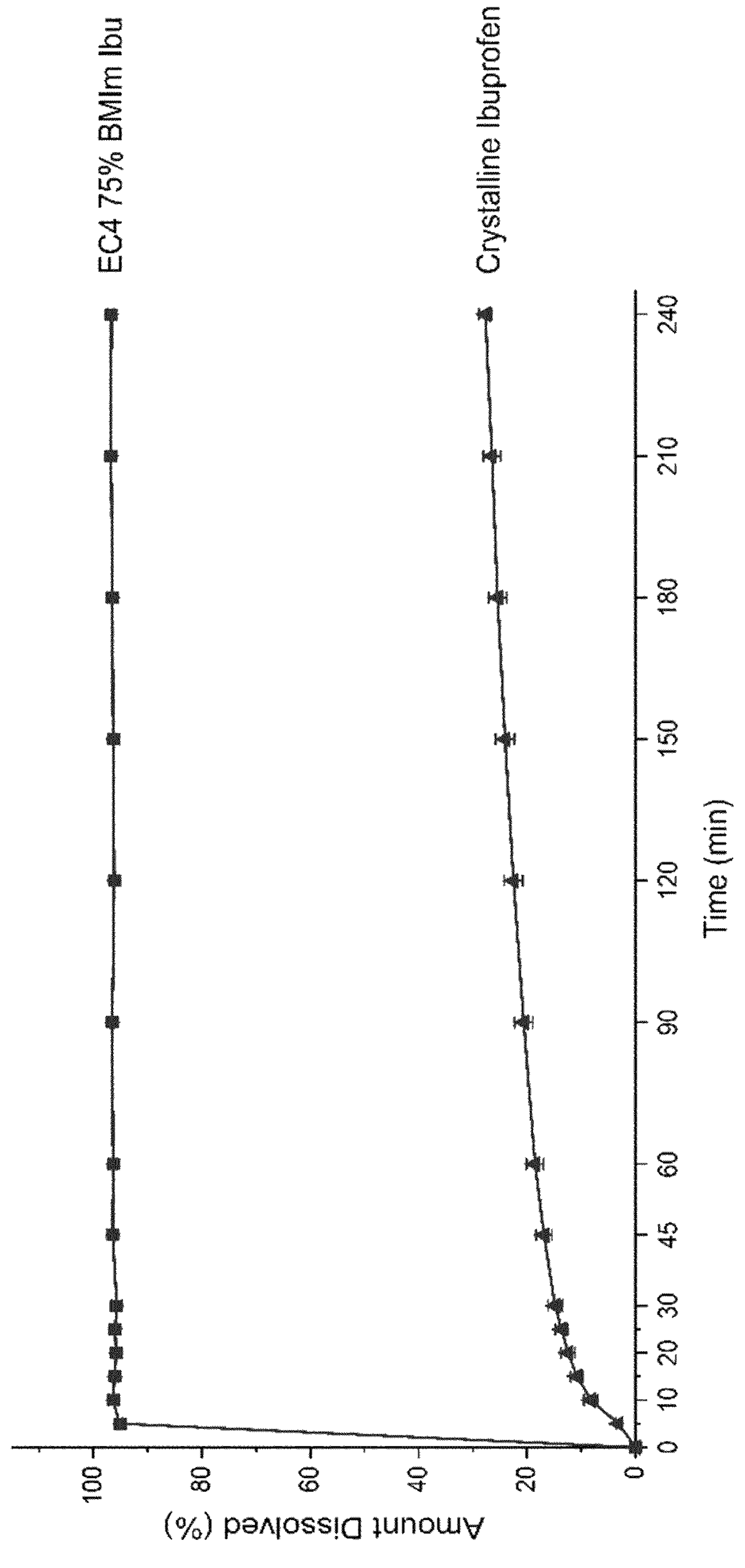
FIG. 27 shows the dissolution profile over time of a spray dried powder comprising 75% w/w BMIm Ibu and 25% w/w EC4 in deionised water compared to crystalline ibuprofen.

The dissolution of powders 9 and 10 in deionised water over a period of four hours was studied. As shown in FIGS. 26 and 27, after 10 minutes and until the end of the four hours, the level of dissolution of the ionic liquid in Powders 9 and 10 was close to 100%. In comparison, under the same conditions crystalline ibuprofen did not achieve more than 30% dissolution.

An ibuprofen amorphous solid dispersion was also tested. The amorphous solid dispersion was prepared by spray drying a solution of ibuprofen and hydroxypropyl methylcellulose in methanol in the same way as Powders 1 to 8. The ibuprofen content of the amorphous solid dispersion was the same as Powder 1. When tested in deionised water in the same way as Powders 1 and 5 to 8, the ibuprofen of the amorphous solid dispersion did not achieve more than 40% dissolution.

The dissolution tests demonstrate the improvement in dissolution performance that is achieved by the compositions of the present invention (comprising a salt of a pharmaceutical compound that is an ionic liquid).

Figure 18:
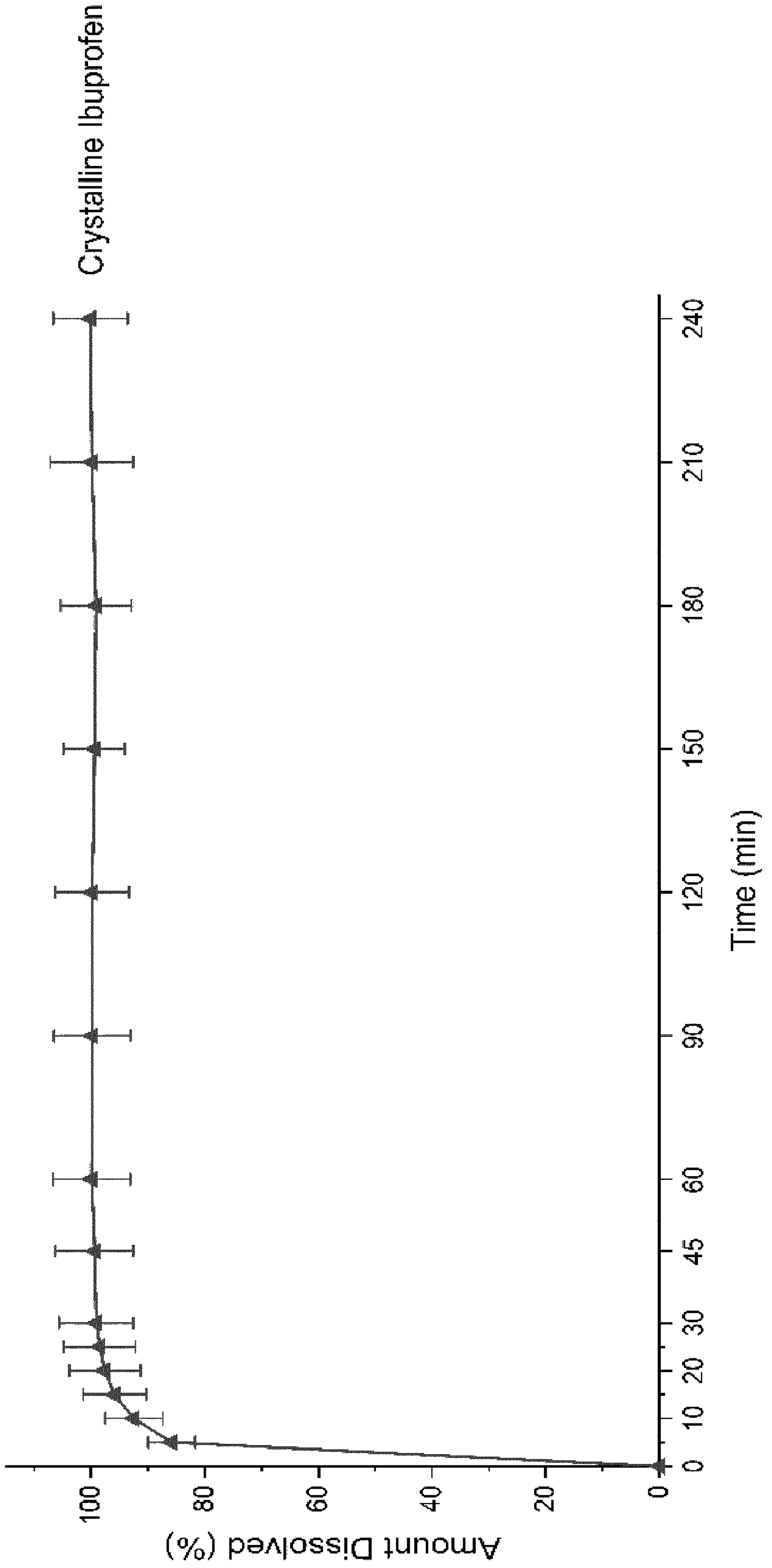
FIG. 18 shows the dissolution profile over time of crystalline ibuprofen in simulated intestinal fluid (SIF), 0.05 M phosphate buffer (pH 6).
Figure 19:
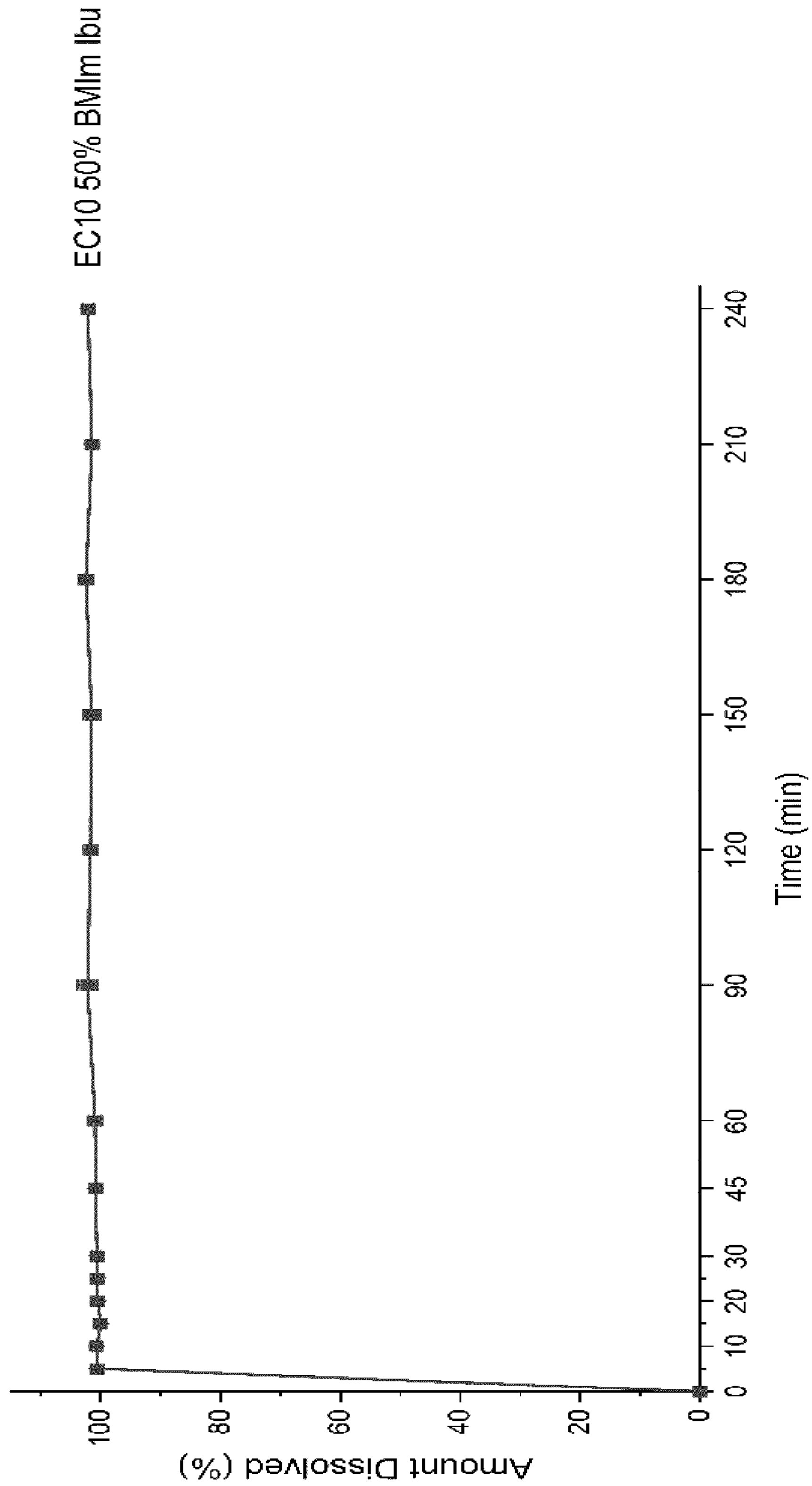
FIG. 19 shows the dissolution profile over time of a spray dried powder comprising 50% w/w BMIm Ibu and 50% w/w EC10 in simulated intestinal fluid (SIF), 0.05 M phosphate buffer (pH 6).
Figure 20:
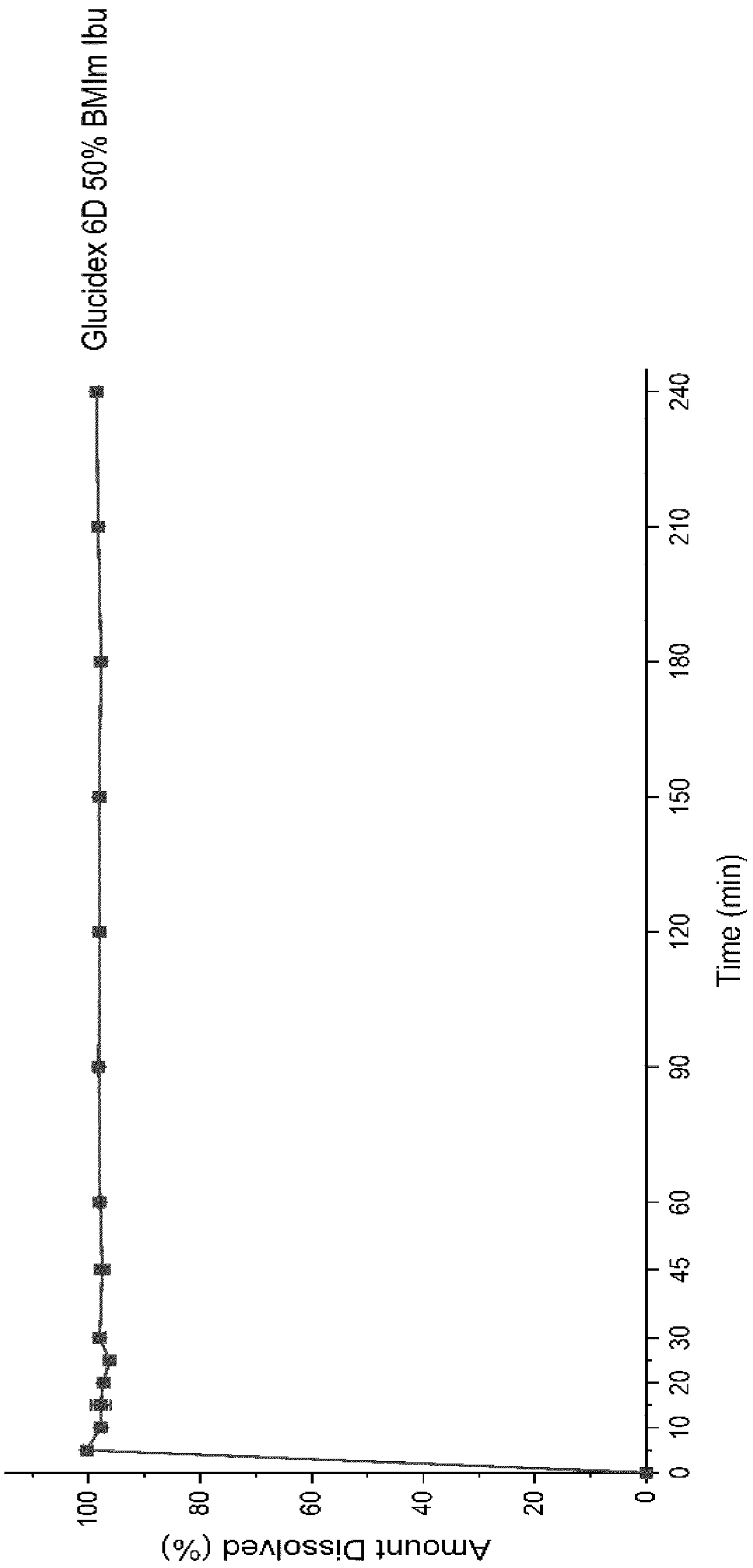
FIG. 20 shows the dissolution profile over time of a spray dried powder comprising 50% w/w BMIm Ibu and 50% w/w Gluc 6D in simulated intestinal fluid (SIF), 0.05 M phosphate buffer (pH 6).
Figure 21:
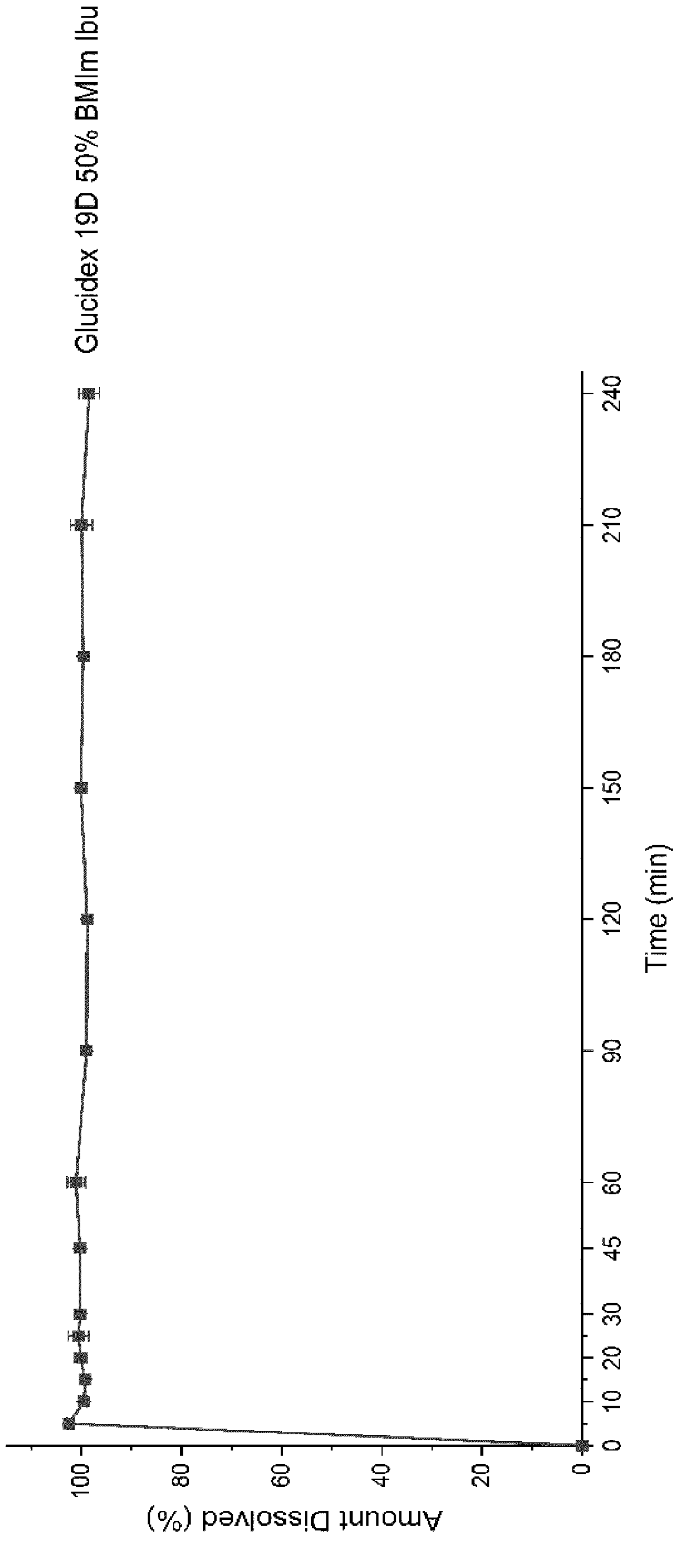
FIG. 21 shows the dissolution profile over time of a spray dried powder comprising 50% w/w BMIm Ibu and 50% w/w Gluc 19D in simulated intestinal fluid (SIF), 0.05 M phosphate buffer (pH 6).
Figure 22:
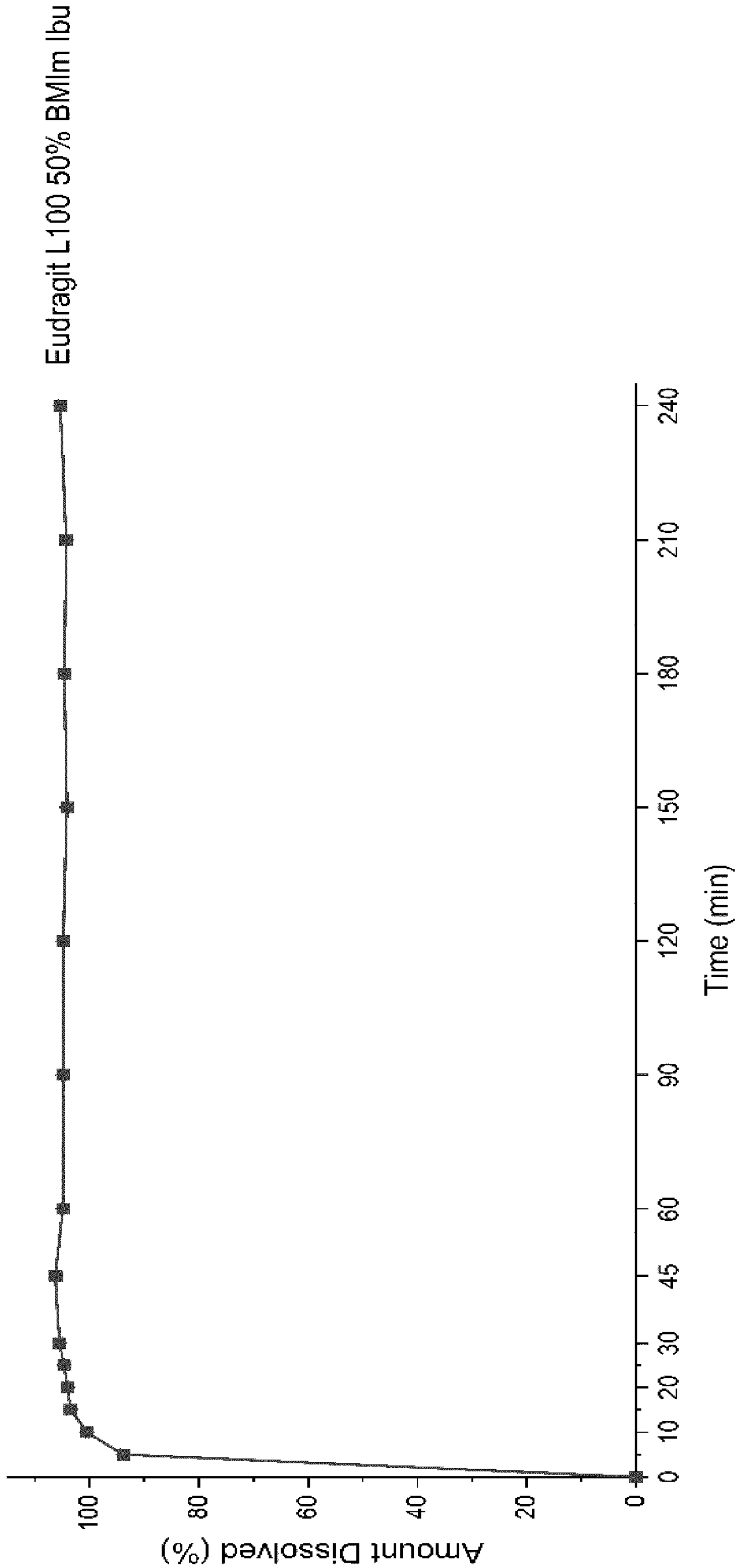
FIG. 22 shows the dissolution profile over time of a spray dried powder comprising 50% w/w BMIm Ibu and 50% w/w Eud L100 in simulated intestinal fluid (SIF), 0.05 M phosphate buffer (pH 6).
Figure 23:
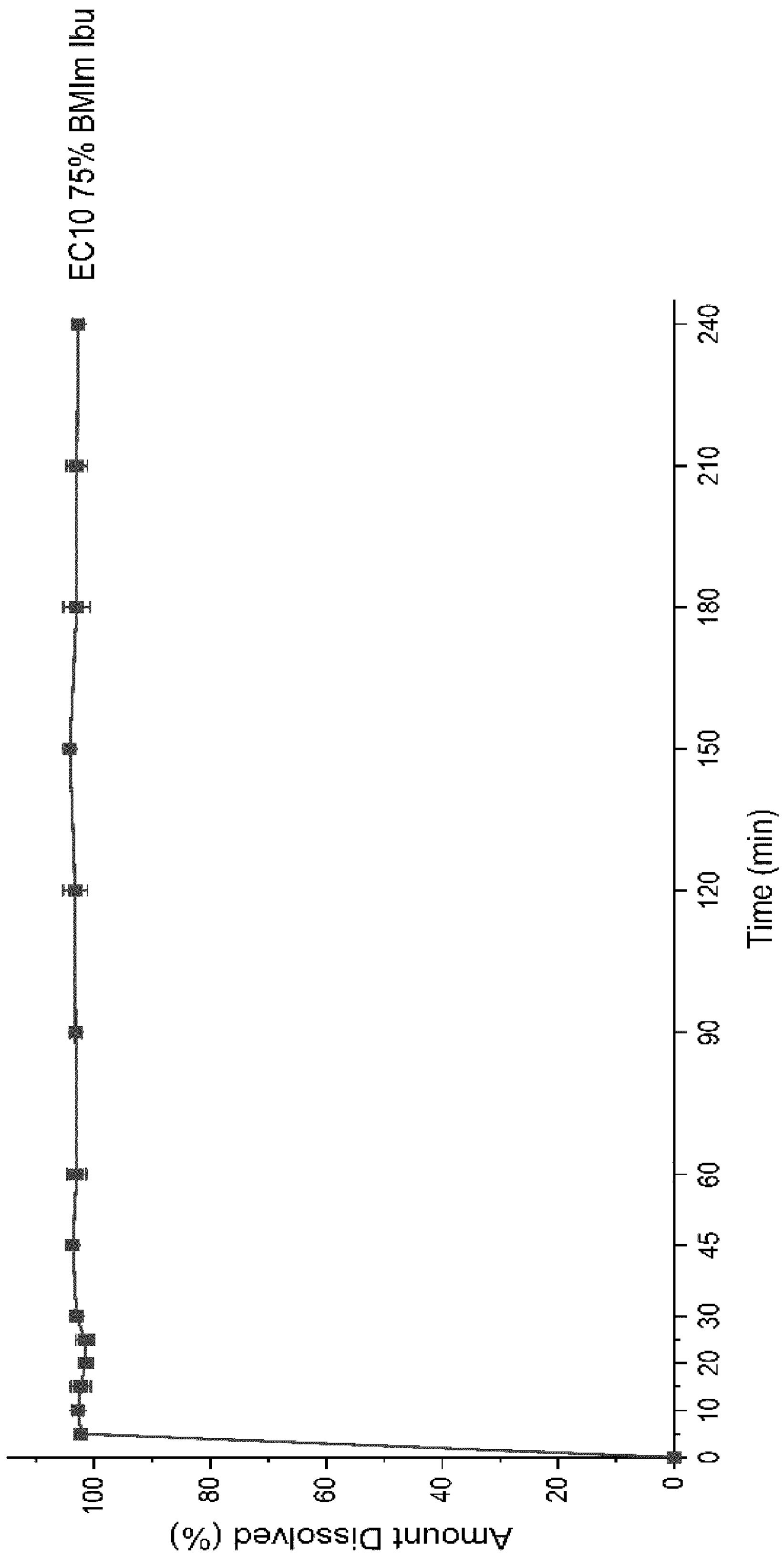
FIG. 23 shows the dissolution profile over time of a spray dried powder comprising 75% w/w BMIm Ibu and 25% w/w EC10 in simulated intestinal fluid (SIF), 0.05 M phosphate buffer (pH 6).

The dissolution of powders 1 and 5 to 8 in simulated intestinal fluid (SIF), 0.05M phosphate buffer (pH 6.8) over a period of four hours was studied. As shown in FIGS. 19 to 23, after 10 minutes and until the end of the four hours, the level of dissolution of the ionic liquid in Powders 1 and 5 to 8 was 100%. As shown in FIG. 18, under the same conditions crystalline ibuprofen also achieved 100% dissolution. This shows that dissolution performance of powders 1 and 5 to 8 was not hindered compared to crystalline ibuprofen.

Figure 28:
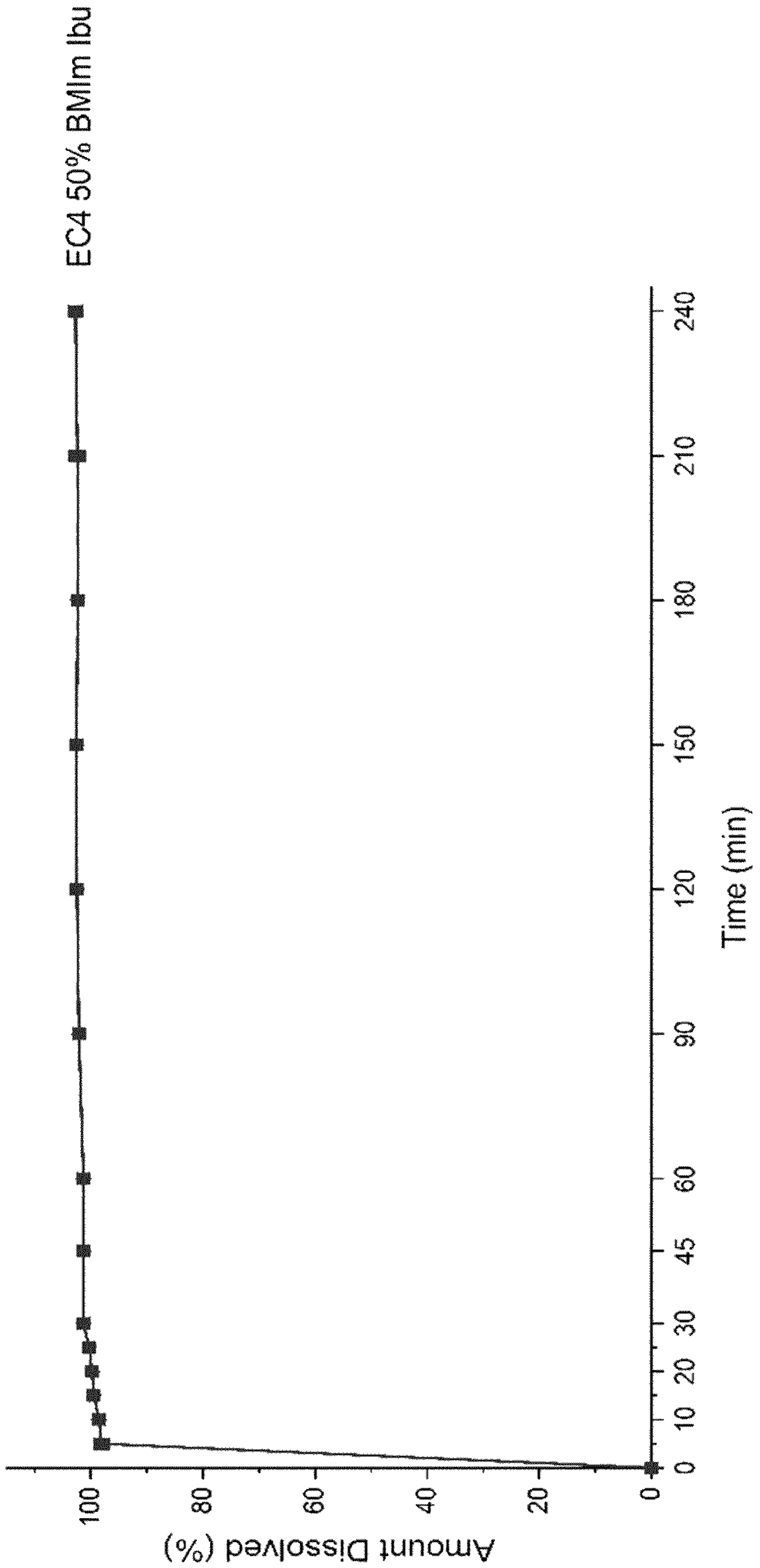
FIG. 28 shows the dissolution profile over time of a spray dried powder comprising 50% w/w BMIm Ibu and 50% w/w EC4 in simulated intestinal fluid (SIF), 0.05 M phosphate buffer (pH 6).
Figure 29:
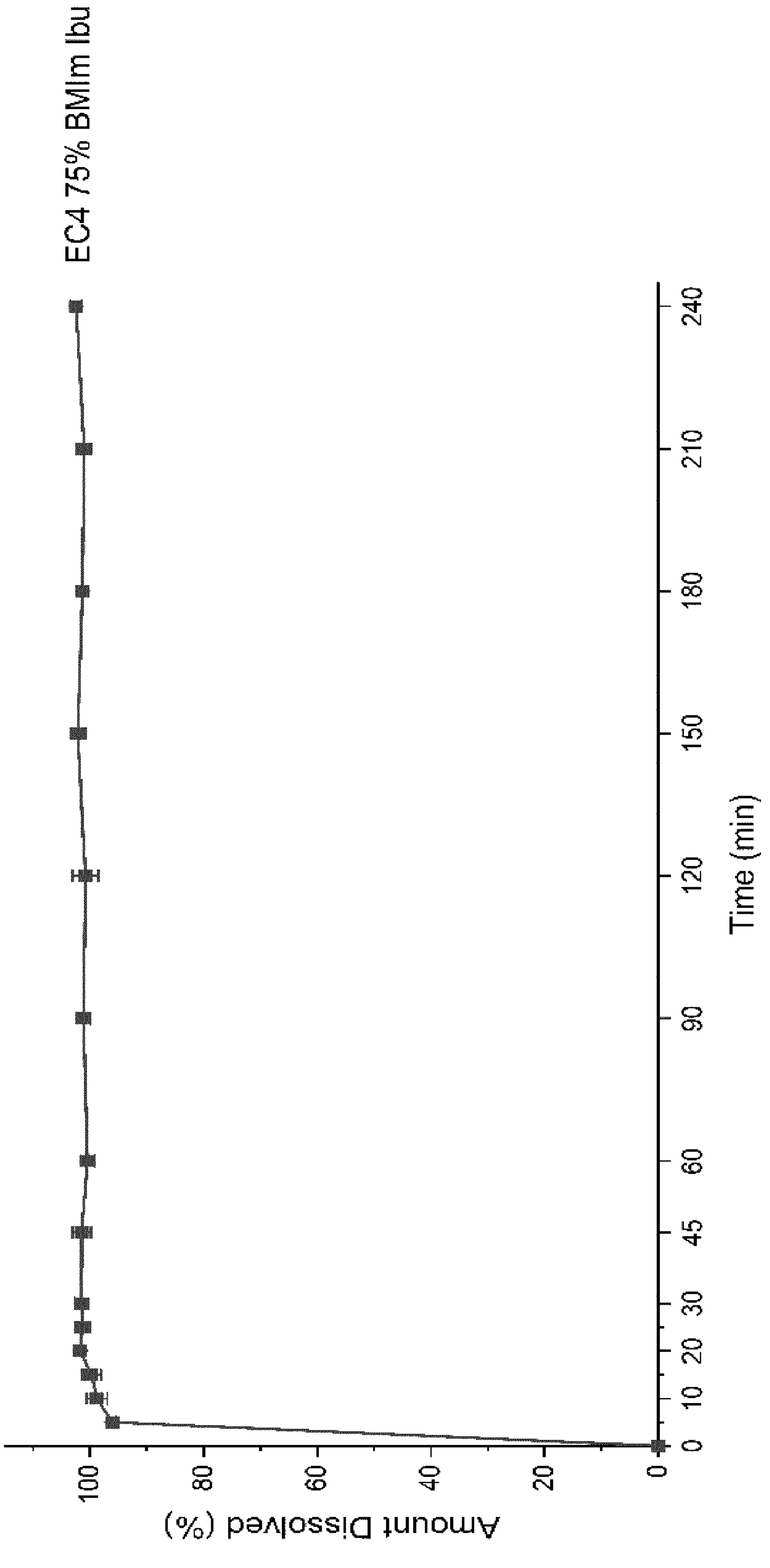
FIG. 29 shows the dissolution profile over time of a spray dried powder comprising 75% w/w BMIm Ibu and 25% w/w EC4 in simulated intestinal fluid (SIF), 0.05 M phosphate buffer (pH 6).

The dissolution of powders 9 and 10 in simulated intestinal fluid (SIF), 0.05M phosphate buffer (pH 6.8) over a period of four hours was studied. As shown in FIGS. 28 and 29, after 10 minutes and until the end of the four hours, the level of dissolution of the ionic liquid in Powders 9 and 10 was 100%. As shown in FIG. 18, under the same conditions crystalline ibuprofen also achieved 100% dissolution. This shows that dissolution performance of powders 9 and 10 was not hindered compared to crystalline ibuprofen.

The example embodiments described above may provide solid compositions comprising pharmaceutical compound containing ionic liquids, which are easy to handle and have good solubility of the pharmaceutical compound. Many pharmaceutical compounds have poor solubility in their most stable crystalline forms, creating problems regarding the bioavailability of the pharmaceutical compound. Non-crystalline forms of pharmaceutical compounds may lack long term stability and/or be in a form which is inconvenient for oral administration. These problems may be addressed by example embodiments as described herein.

In summary, a composition comprising a polymer and a salt of a pharmaceutical compound, wherein the salt is an ionic liquid is described. A solid dosage form comprising such a composition, and a method of preparing the composition are also described. The compositions of the invention have the advantages of long-term stability and bioavailability associated with ionic liquids, and ease of handling and administration associated with solid compositions.

Although a few preferred embodiments have been shown and described, it will be appreciated by those skilled in the art that various changes and modifications might be made without departing from the scope of the invention, as defined in the appended claims.

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention. Typically, when referring to compositions, a composition consisting essentially of a set of components will comprise less than 5% by weight, typically less than 3% by weight, more typically less than 1% by weight of non-specified components.

The term "consisting of" or "consists of" means including the components specified but excluding addition of other components.

Whenever appropriate, depending upon the context, the use of the term "comprises" or "comprising" may also be taken to encompass or include the meaning "consists essentially of" or "consisting essentially of", and may also be taken to include the meaning "consists of" or "consisting of".

For the avoidance of doubt, where amounts of components in a composition are described in wt %, this means the weight percentage of the specified component in relation to the whole composition referred to. For example, "wherein the composition comprises solvents in an amount of less than 10 wt %" means that less than 10 wt % of the composition is provided by solvents.

The optional features set out herein may be used either individually or in combination with each other where appropriate and particularly in the combinations as set out in the accompanying claims. The optional features for each aspect or exemplary embodiment of the invention as set out herein are also to be read as applicable to any other aspect or exemplary embodiments of the invention, where appropriate. In other words, the skilled person reading this specification should consider the optional features for each exemplary embodiment of the invention as interchangeable and combinable between different exemplary embodiments.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, and drawings), or to any novel one, or any novel combination, of the steps of any method or process so disclosed.

The invention claimed is:

1. A solid composition comprising a polymer and a salt of a pharmaceutical compound, wherein the salt is an ionic liquid and the composition is in the form of a powder.

2. The composition of claim 1, which is a solid composition at room temperature.

3. The composition of claim 1, wherein the polymer is immiscible with the ionic liquid at room temperature.

4. The composition of claim 1, wherein the polymer is miscible with the ionic liquid at room temperature.

5. The composition of claim 1, wherein the polymer is selected from a polysaccharide, a polyvinyl ester, an aliphatic polyester, a polyester, shellac, a cellulose derivative, a (meth)acrylic acid based polymer, and mixtures thereof.

6. The composition of claim 1, wherein the salt of a pharmaceutical compound has high solubility as per the Biopharmaceutics Classification System.

7. The composition of claim 1, wherein the free acid or free base of the pharmaceutical compound has low solubility as per the Biopharmaceutics Classification System.

8. The composition of claim 1, wherein the ionic liquid has a melting point of less than 40° C.

9. The composition of claim 1, wherein the polymer has a glass transition temperature of greater than 80° C.

10. The composition of claim 1, wherein the weight ratio of the ionic liquid to the polymer is from 40:60 to 90:10.

* * * * *